(12) United States Patent
Bohm et al.

(10) Patent No.: US 12,157,884 B2
(45) Date of Patent: Dec. 3, 2024

(54) METHOD OF GENERATING TARGETED DNA LIBRARIES

(71) Applicant: Trustees of Tufts College, Medford, MA (US)

(72) Inventors: Alex A. Bohm, Newton, MA (US); Gretchen Meinke, Sharon, MA (US); Nahide Dalda, Dietenbach (DE)

(73) Assignee: Trustees of Tufts College, Medford, MA (US)

( * ) Notice: Subject to any disclaimer, the term of this patent is extended or adjusted under 35 U.S.C. 154(b) by 173 days.

(21) Appl. No.: 17/545,612

(22) Filed: Dec. 8, 2021

(65) Prior Publication Data

US 2022/0177869 A1    Jun. 9, 2022

Related U.S. Application Data

(60) Provisional application No. 63/122,670, filed on Dec. 8, 2020.

(51) Int. Cl.
    *C12N 15/10*    (2006.01)
    *C12N 9/12*     (2006.01)
    *C12Q 1/6806*   (2018.01)

(52) U.S. Cl.
    CPC ....... *C12N 15/1031* (2013.01); *C12N 9/1252* (2013.01); *C12N 15/1093* (2013.01); *C12Q 1/6806* (2013.01); *C12Y 207/07007* (2013.01)

(58) Field of Classification Search
    None
    See application file for complete search history.

(56) References Cited

U.S. PATENT DOCUMENTS

| | | | | |
|---|---|---|---|---|
| 8,685,676 B2 * | 4/2014 | Hogrefe | .................... | C12N 9/22 435/6.12 |
| 2004/0077090 A1 * | 4/2004 | Short | .................. | C12N 15/1027 435/254.2 |
| 2016/0017410 A1 * | 1/2016 | Shendure | ............. | C12N 15/102 506/26 |
| 2021/0032702 A1 * | 2/2021 | Bernstein | ............. | C12Q 1/6881 |

OTHER PUBLICATIONS

Boudsocq et al. "Sulfolobus solfataricus P2 DNA polymerase IV (Dpo4): an archaeal DinB-like DNA polymerase with lesion-bypass properties akin to eukaryotic poleta". Nucleic Acids Research vol. 29, No. 22, p. 4607-4616, published Nov. 15, 2001 (Year: 2001).*
Shivange, Amol V., et al. "Advances in generating functional diversity for directed protein evolution." Current opinion in chemical biology 13.1 (2009): 19-25.
Chaparro-Riggers, Javier F., Karen M. Polizzi, and Andreas S. Bommarius. "Better library design: data-driven protein engineering." Biotechnology Journal: Healthcare Nutrition Technology 2.2 (2007): 180-191.
Bendl, Jaroslav, et al. "HotSpot Wizard 2.0: automated design of site-specific mutations and smart libraries in protein engineering." Nucleic acids research 44.W1 (2016): W479-W487.
Musil, Milos, et al. "FireProt: web server for automated design of thermostable proteins." Nucleic acids research 45.W1 (2017): W393-W399.
Panigrahi, Priyabrata, et al. "Engineering proteins for thermostability with iRDP web server." PloS one 10.10 (2015): e0139486.
Sumbalova, Lenka, et al. "HotSpot Wizard 3.0: web server for automated design of mutations and smart libraries based on sequence input information." Nucleic acids research 46.W1 (2018): W356-W362.
Barnes, Wayne M., and Elaine R. Frawley. "Streamlined gene assembly PCR." Cold Spring Harbor Protocols Mar. 2008 (2008): pdb-prot4862.
Acevedo-Rocha, Carlos G., and Manfred T. Reetz. "Assembly of Designed Oligonucleotides: a useful tool in synthetic biology for creating high-quality combinatorial DNA libraries." Directed Evolution Library Creation: Methods and Protocols (2014): 189-206.
Zeng, Fanli, et al. "AFEAP cloning: a precise and efficient method for large DNA sequence assembly." BMC biotechnology 17.1 (2017): 1-8.
Zeng, Fanli, et al. "Efficient strategy for introducing large and multiple changes in plasmid DNA." Scientific reports 8.1 (2018): 1714.
Gibson, Daniel G., et al. "Enzymatic assembly of DNA molecules up to several hundred kilobases." Nature methods 6.5 (2009): 343-345.
Hidalgo, Aurelio, Anna Schließmann, and Uwe T. Bornscheuer. "One-pot Simple methodology for CAssette Randomization and Recombination for focused directed evolution (OSCARR)." Directed Evolution Library Creation: Methods and Protocols (2014): 207-212.
Goh, Kian Mau, et al. "Use of megaprimer and overlapping extension PCR (OE-PCR) to mutagenize and enhance cyclodextrin glucosyltransferase (CGTase) function." In Vitro Mutagenesis: Methods and Protocols (2017): 385-396.
Caucheteur, Déborah, et al. "Construction of synthetic antibody libraries." Antibody Engineering: Methods and Protocols (2018): 93-108.
Kunkel, Thomas A. "Rapid and efficient site-specific mutagenesis without phenotypic selection." Proceedings of the National Academy of Sciences 82.2 (1985): 488-492.

(Continued)

*Primary Examiner* — Nancy J Leith
*Assistant Examiner* — Jessica D Parisi
(74) *Attorney, Agent, or Firm* — Quarles & Brady LLP

(57) ABSTRACT

The present invention provides methods and kits for efficiently generating edited DNA, ranging from DNA molecules with simple point mutations to complex DNA libraries. The methods and kits use a single-stranded deoxyuridine (dU)-containing template to align a series of DNA oligomers that contain mutations relative to the template strand, giving rise to the sequence variation in the product. The methods and kits may be used to produce DNA libraries or to generate multiple, widely spaced mutations in a target sequence.

12 Claims, 11 Drawing Sheets
Specification includes a Sequence Listing.

(56) References Cited

OTHER PUBLICATIONS

Tang, Lixia, et al. "MDC-Analyzer: a novel degenerate primer design tool for the construction of intelligent mutagenesis libraries with contiguous sites." Biotechniques 56.6 (2014): 301-310.
Strohl, William R. "Current progress in innovative engineered antibodies." Protein & cell 9.1 (2018): 86-120.
Huston, James S., et al. "Protein engineering of antibody binding sites: recovery of specific activity in an anti-digoxin single-chain Fv analogue produced in *Escherichia coli*." Proceedings of the National Academy of Sciences 85.16 (1988): 5879-5883.
Lai, Jing Yi, et al. "Cassette hybridization for vector assembly application in antibody chain shuffling." BioTechniques 65.5 (2018): 269-274.
Sblattero, Daniele, and Andrew Bradbury. "Exploiting recombination in single bacteria to make large phage antibody libraries." Nature biotechnology 18.1 (2000): 75-80.
Krummel, Matthew F., and James P. Allison. "CD28 and CTLA-4 have opposing effects on the response of T cells to stimulation." The Journal of experimental medicine 182.2 (1995): 459-465.
Larkin, James, et al. "Combined nivolumab and ipilimumab or monotherapy in untreated melanoma." New England Journal of medicine 373.1 (2015): 23-34.
Duffy, Austin G., et al. "Tremelimumab in combination with ablation in patients with advanced hepatocellular carcinoma." Journal of hepatology 66.3 (2017): 545-551.
Rizvi, Naiyer A., et al. "Durvalumab with or without tremelimumab vs standard chemotherapy in first-line treatment of metastatic non-small cell lung cancer: the MYSTIC phase 3 randomized clinical trial." JAMA oncology 6.5 (2020): 661-674.
He, Mengnan, et al. "Remarkably similar CTLA-4 binding properties of therapeutic ipilimumab and tremelimumab antibodies." Oncotarget 8.40 (2017): 67129.
Lee, Ju Yeon, et al. "Structural basis of checkpoint blockade by monoclonal antibodies in cancer immunotherapy." Nature communications 7.1 (2016): 13354.
Tang, Lixia, et al. "Construction of "small-intelligent" focused mutagenesis libraries using well-designed combinatorial degenerate primers." Biotechniques 52.3 (2012): 149-158.
Reetz, Manfred T., and Sheng Wu. "Greatly reduced amino acid alphabets in directed evolution: making the right choice for saturation mutagenesis at homologous enzyme positions." Chemical Communications 43 (2008): 5499-5501.
Mena, Marco A., and Patrick S. Daugherty. "Automated design of degenerate codon libraries." Protein Engineering Design and Selection 18.12 (2005): 559-561.
Coco, Wayne M. "RACHITT: Gene family shuffling by random chimeragenesis on transient templates." Directed Evolution Library Creation: Methods and Protocols (2003): 111-127.
Seyfang, Andreas, and Jean Huaqian Jin. "Multiple site-directed mutagenesis of more than 10 sites simultaneously and in a single round." Analytical biochemistry 324.2 (2004): 285-291.
Lipovsek, Dasa, and Pluckthun, Andreas. "In-vitro protein evolution by ribosome display and mRNA display." Journal of Immunological Methods 290 (2004): 51-67.

* cited by examiner

Figure 7

Gene: Cre recombinase
Top strand: SEQ ID NO:43
Bottom strand: SEQ ID NO:44

METHOD OF GENERATING TARGETED DNA LIBRARIES

CROSS-REFERENCE TO RELATED APPLICATIONS

This application claims priority to U.S. Provisional Application No. 63/122,670 filed on Dec. 8, 2020, the contents of which are incorporated by reference in their entireties.

STATEMENT REGARDING FEDERALLY SPONSORED RESEARCH

This invention was made with government support under grants GM126149 and AI150499 awarded by the National Institutes of Health. The government has certain rights in the invention.

SEQUENCE LISTING

A Sequence Listing accompanies this application and is submitted as an ASCII text file of the sequence listing named "166118_01130_ST25.txt" which is 14,911 bytes in size and was created on Dec. 7, 2021. The sequence listing is electronically submitted via EFS-Web with the application and is incorporated herein by reference in its entirety.

BACKGROUND

Error-prone PCR and other completely random mutagenesis schemes are highly inefficient methods for identifying mutations that enhance or alter protein function. Simple probability calculations show that such screens are heavily biased toward amino acids with codons that differ by one or two bases compared to the starting sequence, and the natural degeneracy of the genetic code dictates that some amino acids are six times more likely than others to be sampled. Moreover, stop signals (which are encoded by three different codons) are statistically more likely to be generated than the 10 amino acids that are encoded by just one or two different codons. Importantly, random screening ignores the vast and ever-growing database of sequence and structural information that might inform the search for well-folded proteins with enhanced or altered activity (1).

While unbiased mutagenesis can facilitate the discovery of mutations that would have been overlooked by more rational approaches, it is often the case that the critical mutations identified through random screening cluster in regions that could have been predicted through sequence and/or structure-based analysis (2). Residues at or near an active site, those close to a biologically important interface, or those involved in functionally important movements are more likely than others to modulate activity. These and other "data driven engineering" principles have been successfully used in many cases to improve enzyme activity, enhance stability, and/or alter specificity (3). In short, while it is usually very difficult to predict precisely which mutation(s) will yield a desired effect, it is often relatively easy to identify the regions within a protein sequence where the likelihood of finding favorable mutations is high. Indeed, in recent years a variety of software tools have been developed to help identify the regions where mutations are likely to be most fruitful (3-6).

The vastness of sequence-space is always a major factor in screening projects. With 19 alternate amino acids at each position, there are 1,900 possible single-site mutations in a 100 amino acid protein. Such a protein has over 2.5 million two-site variants and over $2 \times 10^{16}$ 5-site variants. Even highly efficient bacterial screens sample far fewer sequences in each selection cycle. As a consequence, the overall sampling tends to be exceptionally sparse, and many promising variants are likely missed. Rationally designed libraries, wherein the genetic variation is concentrated at specific regions help circumvent many of these issues. The physical construction of such libraries, however, can present a bottleneck in the protein engineering process. This is especially the case if one wishes to achieve relatively uniform sampling of the desired sequence-space and there are multiple and widely spaced regions within the sequence that one wishes to vary.

The problem of synthesizing targeted DNA libraries has been approached in a variety of ways. Many methods rely on some form of gene assembly where a series of overlapping fragments are assembled to form the final product (7). In the 'Assembly of Designed Oligonucleotides (ADO)' approach (8), synthetic overlapping oligonucleotides with variable regions are designed so that there are single-stranded gaps in the assembly in the regions that are being varied. Thus, a polymerase used to fill these gaps generates the complementary strand in the variable regions. In this case, the product is formed in a single reaction, but oligos covering the entire gene are required. Another set of recently reported approaches, termed 'Ligation of Fragment Ends After PCR (LFEAP)' and 'Assembly of Fragment Ends After PCR (AFEAP)' involve two PCR cycles per mutation and results in PCR products with overhangs at each end, which self-assemble to form the final product (9, 10). This utilizes fewer primers than ADO but is still not ideal because two PCR reactions are required for every fragment in the gene assembly. New England Biolab's HiFi Assembly and other 'Gibson assembly' approaches are conceptually similar but require just one set of primers for each mutation. With these approaches, the overhangs required for assembly are generated using an exonuclease (11). Though these approaches require fewer oligos than ADO and the individual fragments can be prepared in parallel, the overall complexity of the procedure (a series of separate PCR reactions, each with specific primers for each mutated region, followed by assembly and usually ligation to form the final product) is still somewhat involved. This is also the case for megaprimer and overlapping extension-based approaches, including OSCARR (One-pot Simple methodology for CAssette Randomization and Recombination) (12). In these approaches, the products of intermediate rounds of PCR are used as primers for subsequent PCR cycles (13).

Thus, most current approaches for making widely spaced multisite libraries require either (a) multiple PCR cycles to generate intermediate products that are later assembled or (b) a single reaction with a collection of primers that spans the entire gene. While these available approaches have been successfully used in a variety of large-scale mutagenesis and protein engineering efforts (2), they are relatively cumbersome, and the intermediate PCR steps make it difficult to control the precise distribution of randomized nucleotides at the mutated sites. As a consequence, some sequences may be oversampled, while others may be completely absent from the resulting library. Thus, there remains a need in the art for efficient, fast, and inexpensive methods for generating targeted DNA libraries.

SUMMARY

The present invention provides methods for generating edited DNA. The methods involve (a) amplifying a template via polymerase chain reaction (PCR) using a first phosphorylated primer, a second non-phosphorylated primer, and a DNA polymerase capable of incorporating deoxyuridine triphosphate (dUTP) to generate a deoxyuridine (dU)-containing amplicon; (b) digesting the dU-containing amplicon of step (a) to degrade the phosphorylated strand and produce a single-stranded, dU-containing template; (c) annealing at least one mutagenic primer to the template of step b, wherein the mutagenic primer is 5' phosphorylated single-stranded DNA comprising an edited region flanked by at least 10 bases that are complementary to the template, and wherein the edited region comprises at least one mutation relative to the complement of the template; (d) extending the mutagenic primers annealed in step c using a DNA polymerase that can read through uracil present in DNA and lacks 3'-exonuclease activity, 5'-exonuclease activity, and strand displacement activity; (e) ligating the extension product of step d to produce a partially mismatched double-stranded DNA product comprising a ligated edited strand and the dU-containing template; and (f) amplifying the edited strand of step e using a forward primer, a reverse primer, and a DNA polymerase.

In another aspect, the present invention provides kits for generating edited DNA. The kits comprise a first DNA polymerase that is capable of incorporating dUTP and reading through uracil present in DNA, and that lacks 3'-exonuclease activity, 5'-exonuclease activity, and strand displacement activity; a second DNA polymerase that is not capable of reading through uracil present in DNA; at least two dNTP mixes, wherein at least one dNTP mix contains dU and at least one dNTP mix does not contain dU; and a lambda (k) exonuclease.

BRIEF DESCRIPTION OF THE DRAWINGS

FIG. 7 shows five SLUPT primers spaced across recombinase gene. The phosphorylated donor primer (purple box) is shown aligned to the recombinase template. The primers are each separated by ~50 bases and were used simultaneously in SLUPT for mutagenesis spread across a gene. Each donor primer changes 3 bases.

DETAILED DESCRIPTION

Figure 1:
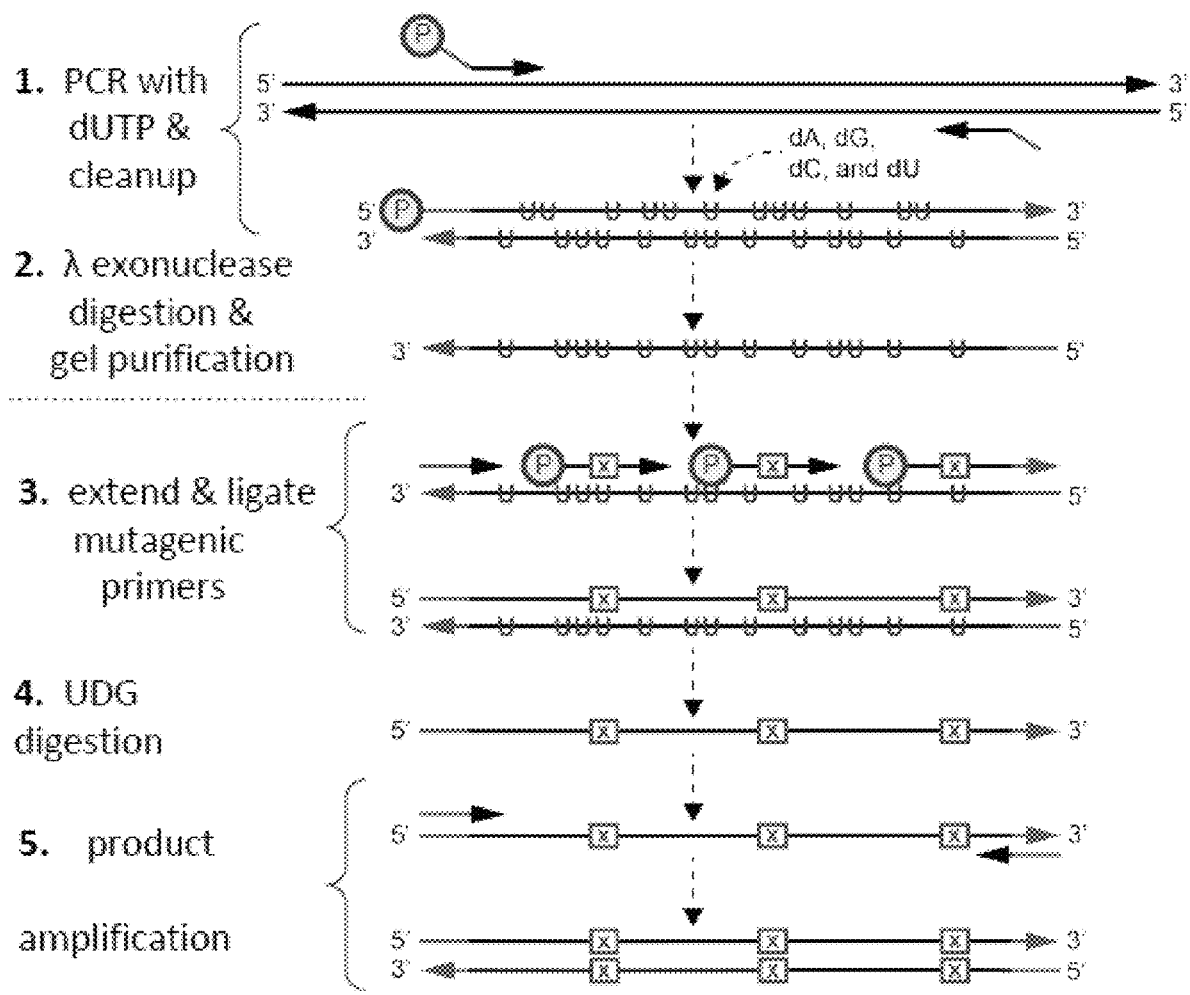
FIG. 1 shows a schematic overview of the SLUPT method. Step 1: The gene of interest is amplified with a 5' phosphorylated top strand primer and dNTPs containing deoxyuridine (dU)(blue). The primer for the bottom strand is not phosphorylated. Optional, nonhomologous regions (e.g., to introduce restriction enzyme sites) are shown in green. Step 2: The phosphorylated strand is selectively degraded by lambda exonuclease to create the uracil-containing single stranded template. Step 3: An end-primer complementary to the 3' terminus and 5' phosphorylated internal primers containing altered bases are annealed to the uracil containing single strand template. Altered bases are depicted as X's in a red box. Gap filling and ligation are performed by Phusion®-U and Taq ligase to create a mutated, complementary strand. Step 4: The Uracil-containing single stranded template is digested by UDG. Step 5: The single-stranded product is made double-stranded and amplified by PCR.

The present invention provides methods and kits for generating edited DNA. In these methods, which the inventors have termed SLUPT (synthesis of libraries via deoxyuridine (dU)-containing PCR templates), a single-stranded dU-containing template is used to align a series of mutagenic primers that contain mismatched bases relative to the template strand (see FIG. 1). These primers are used to produce a product strand that comprises mutations in targeted regions. The dU template is then enzymatically degraded leaving only the product strand, which is amplified by PCR. Thus, the SLUPT method can be used to quickly construct highly targeted DNA libraries with mutated regions that may be close to or far from one another in the template sequence. Advantageously, the alternative nucleotides at the varied positions are stoichiometrically well balanced in the DNA libraries produced by SLUPT. As a result, this method is well-suited for engineering efforts in which having all the sequences within the library at the same concentration maximizes the number of protein variants that can be effectively screened. SLUPT can also be used to efficiently make multiple, simultaneous, specific substitutions within a target sequence.

The SLUPT method is an improvement as compared to earlier methods such as RACHITT (36), the multisite mutagenesis method described by Seyfang and Jin (18), QuikChange® Multi Site-Directed Mutagenesis (Invitrogen), and Kunkel mutagenesis (15).

RACHITT (random chimeragenesis on transient templates) is a DNA sequence shuffling method in which a single-stranded dU-containing template is used to align relatively large fragments of DNA homologs of a gene of interest (36). The SLUPT method is distinct from RACHITT in that RACHITT cannot be used with synthetic primers that contain targeted mutations because the 5' exonuclease activity of the polymerase used with the method degrades the primers.

The multisite mutagenesis method described by Seyfang and Jin uses a conventional single-stranded DNA template to align a series of mutation-containing primers (18). However, this method is significantly less efficient than the SLUPT method, and it does not involve degradation of the nontemplate strand or inactivation of the template after the product strand has been synthesized.

Figure 3A:
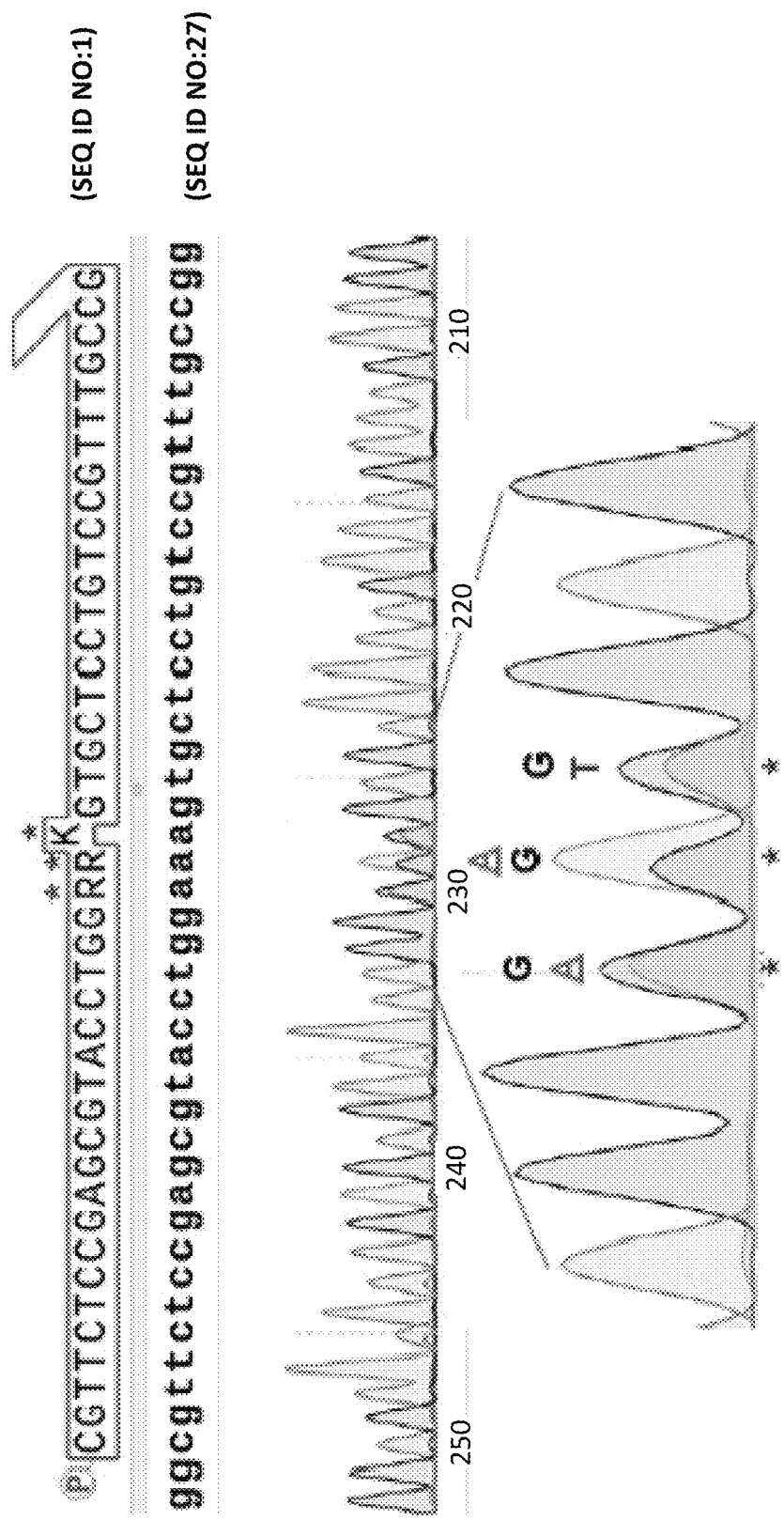
FIG. 3 shows exemplary sequencing results of the amplified library wherein two mutated regions are separated by ~130 bp. Sanger sequencing chromatograms of the library in the mutated helix B region (A) and the mutated helix D region (B) of the recombinase. The 5' phosphorylated donor primer is shown in a purple box above the starting sequence (lowercase, bold). The location of the mutations within the primer are indicated by a *. An expanded view of the mutated region is shown, and the mutated bases are listed in order of their approximate peak height and the bases are colored according to their corresponding trace. Underlined bases are those that correspond to the starting sequence. The red arrow in B denotes a simple G>A base substitution. The library shown in C is identical to that shown in B, but the primers and template were heated to 95° C. and then allowed to cool before the elongation/ligation step. Positions where the templated base are strongly favored are marked with blue triangles.
Figure 3B:
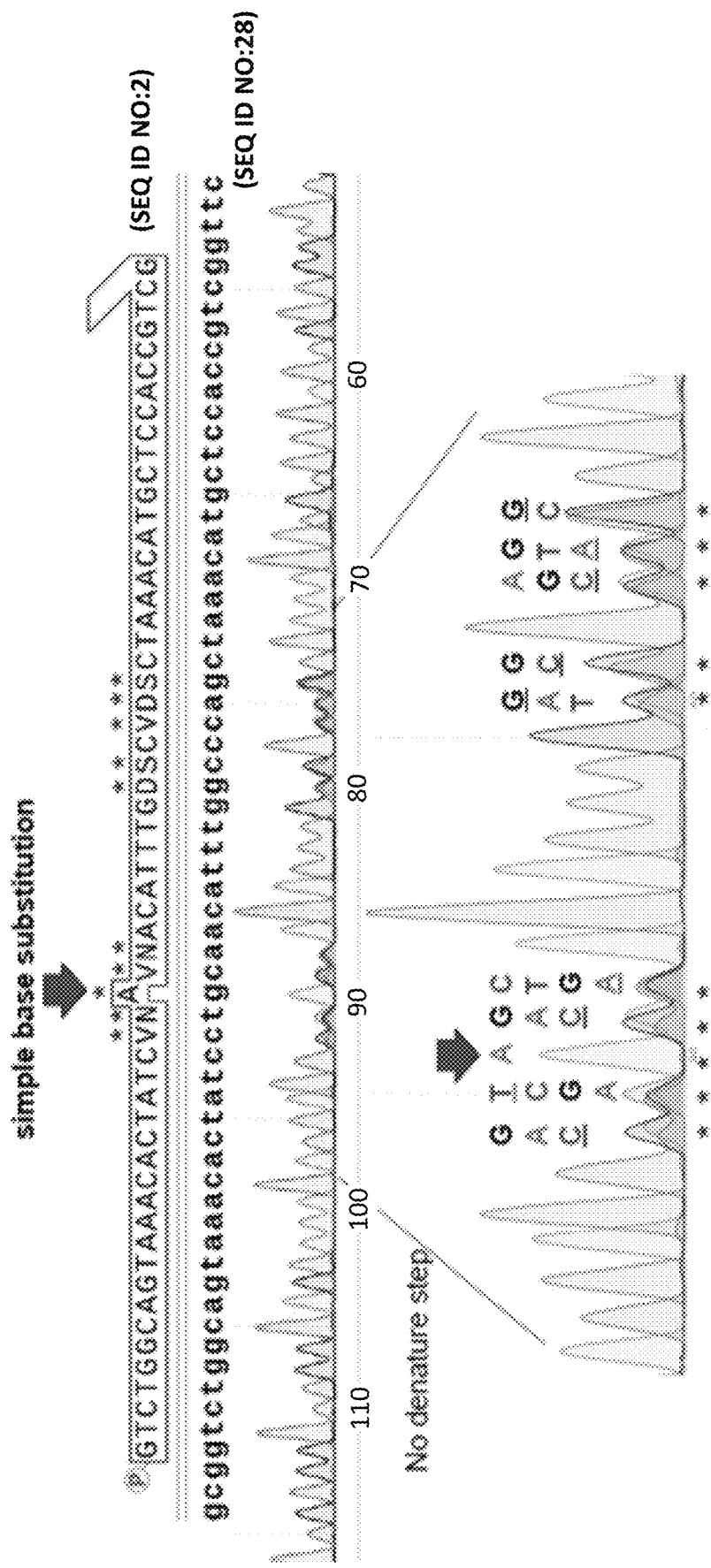
Figure 3C:
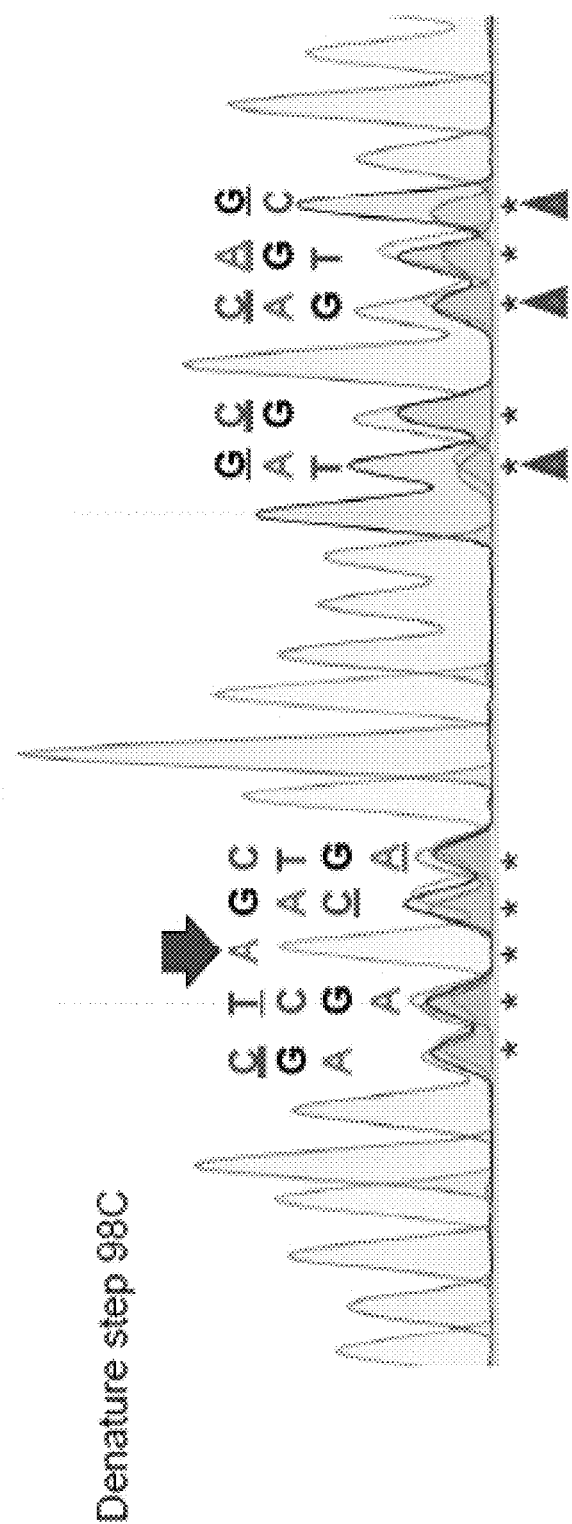

The QuikChange® Multi Site-Directed Mutagenesis method (Invitrogen) offers many of the same advantages as the SLUPT method. However, in QuikChange® method, the nontemplate strand can compete with the mutagenic primers as no effort is made to remove it from the reaction, and our SLUPT experiments indicate that the DNA melting step prior to primer annealing likely enhances primer competition for the template and hinders a uniform distribution of bases in the product strands (see FIG. 3C).

The Kunkel mutagenesis approach relies on the use of M13 phage to generate a single-stranded template and the use of a dut ung *E. coli* strain that occasionally incorporates the RNA base uracil into this template. See e.g. Caucheteur et al. (14, 15). As in the SLUPT method, genetic variation is introduced via primers that contain degenerate bases. These primers are extended and ligated to form the product strand. The major difference between this method and the SLUPT method is that, in the SLUPT method, the single-stranded template is made by PCR. This simplifies the process of template preparation considerably. Further, the Kunkel method is somewhat cumbersome because it requires a special strain of bacteria, phage infection, and phage DNA isolation prior to library synthesis.

Relative to these earlier methods, SLUPT simplifies the process of generating the template and eliminates the heating step prior to primer annealing, which likely leads to more uniform sampling as described in the examples. Another key advantage of the SLUPT method is that it uses the high-fidelity polymerase Phusion® U for primer extension. This enzyme has three key features: (1) it lacks 5' exonuclease and strand displacement activity, (2) it is active on a dU-containing template, and (3) it has a low error rate. Thus, this polymerase enables highly efficient library generation using the methods disclosed herein. Other critical differences that distinguish the SLUPT method from these earlier methods include the use of phosphorylated mutagenic primers and the method of annealing.

Methods

Conceptually, the SLUPT method of the present invention may be broken into six steps: (a) amplifying a template via polymerase chain reaction (PCR) using a first phosphorylated primer, a second nonphosphorylated primer, and a DNA polymerase capable of incorporating deoxyuridine triphosphate (dUTP) to generate a dU-containing amplicon; (b) digesting the dU-containing amplicon of Step A to degrade the phosphorylated strand and produce a single-stranded, dU-containing template; (c) annealing at least one mutagenic primer to the template of Step B, wherein the mutagenic primer is 5' phosphorylated single-stranded DNA comprising an edited region flanked by at least 10 bases that are complementary to the template, and wherein the edited region comprises at least one mutation relative to the complement of the template; (d) extending the mutagenic primers annealed in Step C using a DNA polymerase that can read through uracil present in DNA and lacks both 5'-exonuclease activity and strand displacement activity to produce an extension product; (e) ligating the extension product of Step D to produce a double-stranded DNA product comprising a ligated edited strand; and (f) amplifying the edited strand of Step E using a forward primer, a reverse primer, and a DNA polymerase. These methods are outlined as a schematic in FIG. 1, in which Step 1 corresponds with Step A, Step 2 corresponds with Step B, Step 3 corresponds with Steps C, D, and E, Step 4 is optional, and Step 5 corresponds with Step F.

Step A: Amplifying a dU-Containing Template

The methods utilize polymerase chain reaction (PCR) to amplify (i.e., produce multiple copies of) DNA. PCR is a popular technique used to amplify nucleic acid (e.g., see U.S. Pat. Nos. 4,683,195 and 4,683,202, as well as Saiki et al., Science 230:1350-1354 (1985) and Gyllensten et al., PNAS (USA) 85:7652-7656 (1985)). Any variation of this amplification technique may be used with the present invention. In its simplest form, PCR is an in vitro method for the enzymatic synthesis of specific DNA sequences, using two primers that hybridize to opposite strands and flank the region of interest in the target DNA. A repetitive series of reaction steps involving template denaturation, primer annealing and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of 109 relative to other sequences in genomic DNA.

PCR is performed using "template DNA" (at least 1 fg; more typically, 1-1000 ng), which is also referred to herein as simply a "template". The template DNA comprises a sequence that is complementary to a DNA fragment of interest, i.e., the target sequence from which the user wants to generate DNA libraries and/or DNA mutants.

The template amplification reaction should also include at least 25 pmol of primers designed to amplify the target sequence. Suitably, the primers are designed such that their melting temperatures are between 55° C. and 65° C. The term "primer", as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

In Step A, the forward primer is phosphorylated on its 5' end, and the reverse primer is not phosphorylated. As used herein, the term "phosphorylated" is used to describe a molecule to which a phosphate group has been added. It is convenient to simply order phosphorylated primers, but primers can also be phosphorylated enzymatically (i.e., using T4 polynucleotide kinase).

PCR also utilizes a "DNA polymerase", an enzyme that catalyzes the polymerization of nucleoside triphosphates. The enzyme will initiate synthesis at the 3'-end of the primer annealed to the target sequence and will proceed in the 5'-direction along the template. Importantly, in place of the usual PCR oligonucleotide mixture, a mixture in which dT is replaced by dU is used with the methods disclosed herein. Such mixtures are commercially available, e.g. from ThermoFisher Scientific. Thus, a DNA polymerase that is able to incorporate dU and is tolerant of dU in the template strand must be used in this step. Suitable DNA polymerase include, without limitation, Taq polymerase (NEB) and Phusion® U Hotstart polymerase (ThermoFisher). Preferably, the polymerase is a high-fidelity DNA polymerase. As used herein, the term "high-fidelity" describes any DNA polymerase that is less error prone than Taq polymerase, which has an error rate of about 2 errors per 3 kb. A high-fidelity polymerase may have an error rate at least 10, 20, 30, 40, 50 or up to 100 fold less than Taq.

For the most part, routine PCR parameters may be used with the methods of the present invention. For example, typical reaction mixture might include: 2 µl of template DNA (e.g., 5-10 ng), 25 pmol of oligonucleotide primer, 2.5 µl of a suitable buffer, 0.4 µl of 1.25 uM dNTP with dUTP, 2.5 units of Taq DNA polymerase (New England Biolabs) and deionized water to a total volume of 25 µl. The precise parameters for the PCR (temperatures, elongation times, and number of cycles) will depend on the primers, the length of the region being amplified, and the concentration of the template. The parameters need not differ from those used in DNA amplification reactions that do not involve the dU for dT substitution.

The PCR step of the present methods are performed in a PCR device such as a programmable thermocycler. The reaction may also be performed under real-time reaction conditions in a real-time PCR device. Real-time reaction conditions further utilize a nucleic acid detection agent (e.g., dye or probe) to measure/detect the PCR product as it is produced. The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 30° C. and 72° C. may be used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above: 1-2 minutes), and extension (72° C. for 1 minute). The final extension step is generally carried out for 4 minutes at 72° C., and may be followed by an indefinite (0-24 hour) hold at 4° C.

The template amplification reaction (Step A) is used to generate a dU-containing amplicon (i.e., amplification product), also referred to herein as the "dU-containing template". Multiple libraries and/or mutant versions of the target sequence may be prepared from this template, making this technique ideally suited for applications where a large number of specific mutations of a target sequence or a large number of different libraries based on the same template are needed. Thus, it may be advantageous to scale-up this amplification step after confirming that the reaction parameters are successful. In some embodiments, the dU-containing amplicon is purified before the amplicon is used in Step B. Suitable methods for purifying a DNA amplicon include, without limitation, gel extraction, ethanol precipitation, phenol-chloroform extraction, and mini-column purification (e.g., using a PCR cleanup kit).

Step B: Producing a Single-Stranded, dU-Containing Template

In the second step of the disclosed methods, the 5'-phosphorylated top strand of the dU-containing amplicon is digested (i.e., cut into smaller pieces) to produce a single-stranded, dU-containing template. In some embodiments, the phosphorylated strand is digested using a lambda (λ) exonuclease, an enzyme that degrades 5'-phosphorylated DNA. Lambda exonuclease is commercially available, e.g., from New England Biolabs and Thermo Fisher Scientific.

In some embodiments, the single-stranded, dU-containing template produced is purified before the template is used in Step C. The molar concentration of the template may also be determined (e.g., by measuring the absorbance at 260 nm), and the sample may be aliquotted and stored at −20° C. (or at −80° C. for long periods). As is detailed in the Examples, validation may be performed to test the quality of template and to determine the minimum amount of template needed for robust product formation. For example, the template may be subjected to UDG digestion and PCR amplification, since after digestion, only contaminating DNA that does not contain dU bases will yield a PCR product.

Step C: Annealing Mutagenic Primer to the Template

In Step C, at least one mutagenic primer is annealed to the single-stranded, dU-containing template. A primer is "annealed" to a template when the nucleotide bases of the primer form hydrogen bonds with the nucleotide bases of the template. As used herein, the terms "mutagenic primer" and "donor primer" are used interchangeably to refer to a primer that has been designed to introduce at least one mutation into a target sequence. The mutagenic primer contains a 5' phosphate, allowing the strands produced by primer extension to be ligated together in Step E. Further, the mutagenic primer should contain at least about 10 base pairs, at least 15 base pairs, at least 16 base pairs, at least 17 base pairs, at least 18 base pairs, at least 19 base pairs, or at least 20 base pairs of DNA that are perfectly complementary to the template on either side of the region being altered, i.e., the edited region). As used herein, the term "complementary" is used interchangeably with the term "reverse complementary" to refer to a nucleic acid sequence that can form a double-stranded structure with another nucleic acid sequence through matching base pairs (e.g., A-T and G-C base pairs). The edited region comprises at least one mutation relative to the complement of the template. Suitable mutations include base insertions, deletions, and substitutions. In some embodiments, the at least one mutagenic primer annealed in this step contains more than one mutation relative to the complement of the template, as to introduce several changes to the target sequence using a single primer. In some embodiments, more than one mutagenic primer is annealed in this step. Notably, multiple mutagenic primers may be used to create mutations at disparate regions of the template. As used herein, the term "disparate regions" refers to regions of a DNA sequence that are separated by at least one nucleotide. Mutated disparate regions may be any distance apart, as there is no limitation regarding how close a pair of mutagenic primer binding sites must be to one another within the context of the template sequence. The only limitation on the distance between mutated regions is that the extension product produced from the template must be amplifiable. The limitations on amplification are dictated by the choice of polymerase. In some embodiments, the annealing step is performed at room temperature (about 21-22° C.).

In some embodiments, an additional "non-mutagenic primer" (i.e., a primer that does not contain mutations relative to the complement of the template) is annealed to the 3' end of the template in Step C. This primer serves to define the 5' end of the product strand. Notably, it does not matter whether this primer is or is not phosphorylated, and it is fine to reuse the phosphorylated "forward" primer from Step A, above. It is also fine to introduce mutations using a different 5' primer. However, when making a library, it may be problematic to introduce DNA variation within the bases near the 5' end of this primer. The bases near the ends must have a well-defined sequence since they will be used in the final PCR amplification step below.

Step D: Extending Mutagenic Primers to Produce an Extension Product

In Step D, the mutagenic primers are extended using a DNA polymerase that can read through uracil present in DNA and lacks both 5'-exonuclease activity and stand displacement activity. Suitably, a high-fidelity DNA polymerase is used in this step. In some embodiments, the DNA polymerase used in Step D is Phusion® U or *Sulfolobus* DNA Polymerase IV. Either of these polymerases can be used to efficiently carry out the U-templated extension while leaving the downstream primers intact. While the high error rate of *Sulfolobus* DNA Polymerase IV makes it unsuitable for highly targeted mutagenesis applications, this feature could possibly be useful for generating large numbers of random mutations in conjunction with targeted mutations.

Step E: Ligation

A DNA ligase is then used to join (i.e., ligate) the fragments created by primer extension together, forming a double-stranded DNA product. A "DNA ligase" is an enzyme that facilitates the joining of DNA strands together by catalyzing the formation of a phosphodiester bond between the 5' phosphate of one strand and the 3' hydroxyl of the other. Suitably, a thermostable ligase (e.g., Taq ligase) is utilized such that the ligation can be performed during PCR, i.e., at the same time as the extension reaction and in the same reaction vessel.

In some embodiments, the methods further comprise digesting the resulting double-stranded DNA product to remove the dU-containing template strand, leaving only the product strand (which does not contain dU nucleotides). In particular embodiments, the digestion is performed using uracil-DNA glycosylate (UDG). UDG is an enzyme that evolved to prevent mutagenesis by eliminating uracil from DNA molecules by cleaving the N-glycosylic bond and initiating the base-excision repair pathway. UDG cleaves the uracil base from the phosphodiester backbone of uracil-containing DNA but has no effect on natural (i.e., thymine-containing) DNA. UDG is commercially available, e.g., from New England Biolabs.

Step F: Amplifying the Edited Strand to Produce a Double-Stranded Product

In the final step, PCR is used to first generate the missing bottom strand and then to amplify the resulting double-stranded DNA product. This reaction requires primers that are homologous to the 3' and 5' ends of the product DNA (i.e. equivalent to the 5'end and complementary to the 3' end). These primers may be the same as those used in Step A. However, if 3' or 5' extensions or deletions are required, the primers can be different than those used in Step A.

Any DNA polymerase may be used in this step. However, it is preferable to use a high-fidelity polymerase. In some embodiments, the DNA polymerase utilized in Step F is not able to read through uracil present in DNA. Using this type of polymerase provides an added measure of security in case the UDG digestion was incomplete, ensuring that the template strand does not contaminate the reaction. Suitable DNA polymerase include, without limitation, Taq polymerase or Phusion® polymerase.

The resulting double-stranded product may be subjected to a purification step. The size and purity of the product may also be verified using an agarose gel. For some applications, it may be important to verify that the desired mutations have been introduced, e.g., by sequencing the product.

Kits

The present invention also provides kits for generating edited DNA. The kits comprise a first DNA polymerase that is capable of incorporating dUTP and reading through uracil present in DNA, and that lacks both 5'-exonuclease activity and stand displacement activity; a second DNA polymerase that is not capable of reading through uracil present in DNA; at least two dNTP mixes, wherein at least one dNTP mix contains dU and at least one dNTP mix does not contain dU; and a lambda (k) exonuclease.

The kits include at least two DNA polymerases: one that is capable of incorporating dUTP and reading through uracil present in DNA and one that is not. In some embodiments, the first DNA polymerase that is capable of incorporating dUTP is Phusion® U or *Sulfolobus* DNA Polymerase IV. In some embodiments, the second DNA polymerase that is not capable is capable of reading through uracil present in DNA Phusion®. However, in some embodiments, the kits further comprise a second, different DNA polymerase that is capable of incorporating dUTP, such that the kits comprise three different DNA polymerases. In the Examples, the inventors use Taq DNA polymerase (New England Biolabs) to amplify the template in Step A, Phusion® U Hotstart polymerase (ThermoFisher) to extend the mutagenic primers in Step D, and Phusion® High-Fidelity DNA Polymerase (New England Biolabs) to amplify the product in Step F. Advantageously, one or more of the polymerases used with the present invention are high-fidelity DNA polymerases.

The kits of the present invention may comprise additional components. In some embodiments, the kits further comprise additional enzymes, such as DNA ligase and uracil-DNA glycosylate, that are useful for practicing the methods disclosed herein. The kits may also include detection reagents, such as a dye that is sensitive to single-stranded DNA. In some embodiments, the kits further comprise instructions for designing and ordering primers for use with the kit. The kits may also comprise additional instructional materials, such as detailed molecular biology directions or helpful hints for designing libraries that enhance the probability of uncovering useful mutations.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

Examples

Directed DNA libraries are useful because they focus genetic diversity in the most important regions within a sequence. Ideally, all sequences in such libraries should appear with the same frequency, and there should be no significant background from the starting sequence. These properties maximize the number of different sequences that can be screened. Described herein is a method, termed "SLUPT" (Synthesis of Libraries via a dU-containing PCR Template), for generating highly targeted DNA libraries and/or multisite mutations, wherein the altered bases may be widely distributed within a target sequence. This method is highly efficient and modular. Moreover, multiple distinct sites, each with one or more base changes, can be altered in a single reaction. There is very low background from the starting sequence, and SLUPT libraries have similar representation of each base at the positions selected for variation. The SLUPT method utilizes a single stranded deoxyuridine (dU)-containing DNA template that is made by PCR. Synthesis of the template in this way is significantly easier than has been described earlier. A series of oligonucleotide primers that are homologous to the template and encode the desired genetic diversity are extended and ligated in a single reaction to form the mutated product sequence or library. After selective inactivation of the template, only the product library is amplified. There are no restrictions on the spacing of the mutagenic primers except that they cannot overlap.

Methods

Part 1: Preparation of dU Containing ssDNA Template Synthesis and purification of the dU-containing template: The wild-type (wt) template for the recombinase studies is 1050 bp in length. This sequence was amplified using dU-containing NTP mixtures (GeneAmp, N8080270) using either Taq DNA polymerase (New England Biolabs, M0267S) or Phusion®-U Hotstart polymerase (ThermoFisher Scientific, F555S), following the manufacturer's protocol. For this step, the forward 5' primer must be 5' phosphorylated, the 3' reverse primer is not. All primers in this study were synthesized at the smallest scale possible (IDT DNA), with standard desalting and no other purification. No special effort was made to ensure that the stoichiometry of bases at degenerate positions within the ordered nucleotides was exactly balanced (the DNA synthesis company was relied on for this). dU-containing PCR product DNA was gel extracted using various kits (Machery-Nagel, New England Biolabs, Zymo) with similar efficiency. The dU-containing PCR reaction was typically repeated using the purified PCR product as template. The second PCR step affords an opportunity for scale-up at this stage by performing multiple PCR reactions (e.g., ten 50 µl reactions). These second PCR reactions are normally cleaned up via spin columns, but gel extraction is recommended if there are multiple bands. For this 1 kb template, ten 50 µl PCR reactions yielded ~20 µg of dU-containing dsDNA.

Digestion of the 5' phosphorylated 'top strand' with Lambda exonuclease: Typically, 2 g of the purified, dU-containing PCR product is digested with Lambda exonuclease, which generates enough product for many subsequent reactions. The reaction contained the dU-PCR product, 4 µl of 10× lambda exonuclease buffer, 10 U lambda exonuclease (New England Biolabs, M0262S), and water to 40 µl. The reaction was incubated at 37° C. for 1.5 h, followed by heat inactivation at 75° C. for 10 min. Typically, multiple 40 µl reactions (i.e., 5-10 reactions) are performed for scale-up. The ssDNA was extracted from an agarose gel made using SYBR Green II RNA gel stain (Invitrogen, S7564) for better visualization of ssDNA. Recovery of ssDNA from gel slice is typically performed using a DNA gel extraction kit (Machery-Nagel, 740609.50). The concentration of the ssDNA was calculated using the standard extinction coefficient of 33 μg/ml and the length of the ssDNA. The ssDNA transient template was stored at −20° C. until ready for use. This should be enough for hundreds of SLUPT reactions.

Testing the ssDNA template: The quality of the ssDNA was assessed by performing standard 25 μl PCR reactions using Taq DNA polymerase, either with or without prior treatment with Antarctic Thermolabile Uracil DNA glycosylase (UDG) (New England Biolabs, M0372S). For this test, a series of 10-fold dilutions of the ssDNA is used as the template: no dilution, 1:10, 1:100, 1:1,000, and 1:10,000. For each dilution, a 10 μl ±UDG reaction, which contains 1 μl 10×UDG reaction buffer, 1 μl ssDNA, ±1 μl UDG, and water to 10 μl, was prepared. The reaction was incubated for 30 minutes at 37° C. Next, standard PCR was performed using primers that anneal to the start and end of the gene for all the dilutions using 1-2 μl of template. No PCR product in the presence of UDG indicates no template contamination. PCR product in the absence of UDG indicates how low a dilution may be used for the next steps.

Part 2: Annealing, Extension, Ligation, and Amplification of the Product DNA

Design of donor primers: The donor primers, which are also referred to herein as "mutagenic primers", should be designed such that their annealing temperature (excluding the mutated region) is above 55° C., and they should contain 15-20 bases on each side of the desired mutated region that are complementary to the template sequence. All donor primers were ordered with a 5' phosphate, as this is needed for the ligation step. No special purification other than standard desalting was requested. The shortest primer tested to date is 29 bp in length. This primer contains a single nucleotide change near the center, flanked by 10 and 18 homologous bases on either side, respectively. The longest primer tested to date is 68 bp in length. This primer contains multiple mutation regions in the center, flanked by 20 and 21 homologous bases, respectively. There is significant flexibility in the primer design but using very short or very long primers may require empirical testing. All successful donor primers used in this study are shown in Table 1, below. Lyophilized donor primers were resuspended in 10 mM Tris pH 8.5 or sterile milliQ water, typically at a 100 μM concentration, and stored at −20° C.

TABLE 1

Mutagenic primers used for variant library and mutagenesis via SLUPT. Bold text indicates the mutated region. Single letter codes are used to denote base mixtures. N is the length of the primer, 5' is the number of bases on the 5' side of the mutation, 3' is the number of bases on the 3' side of the mutation.

| Donor primer name | 5'→3' donor primer sequences (all are 5' phosphorylated) | N | 5' | 3' |
|---|---|---|---|---|
| Cre Library 1 | | | | |
| helixB | CGTTCTCCGAGCGTACCTGGRRKGTGCTCCTGTCCGTTTGCCG (SEQ ID NO: 1) | 43 | 20 | 20 |
| helixD | GTCTGGCAGTAAACACTATCVNAVNACATTTGDSCVDSCTAAACATGCTCCACCGTCG (SEQ ID NO: 2) | 58 | 20 | 20 |
| helixD (shorter) | GCAGTAAACACTATCVNAVNACATTTGDSCVDSCTAAACATGCTCCAC (SEQ ID NO: 3) | 48 | 15 | 15 |
| Cre Library 2 | | | | |
| region 1 | GATCGCCAGGCGTTCBMAGAGVVTACCTGGVRAVDKCTCCTGTCCGTTTGC (SEQ ID NO: 4) | 51 | 15 | 15 |
| region 2 | GGCTCGCGGTCTGGCAGTAAVWACTATCCTGWVACATTTGGCCCAGCTAAACAT (SEQ ID NO: 5) | 54 | 20 | 21 |
| region 3 | ATAACACCCTGTTACGCGTARVTGAAATTGCCAGGATTCGGAT (SEQ ID NO: 6) | 43 | 20 | 20 |
| region 4 | CCAAGGATGGCTCTGGTCAGCRATACCTGGCCTGGTCTGGGCA (SEQ ID NO: 7) | 43 | 20 | 21 |
| Mutations | | | | |
| 1 bp change | CCTGATGGATATGCTCAGGGATCGCCAGG (SEQ ID NO: 8) | 29 | 10 | 18 |
| 1 bp deletion | CTCGCAAGAACCTGATG-ATGTGCTCAGGGATCGCC (SEQ ID NO: 9) | 35 | 17 | 18 |
| 1 bp insertion | CTCGCAAGAACCTGATGGATCGTGCTCAGGGATCGCC (SEQ ID NO: 10) | 37 | 20 | 16 |
| 9 bp insertion | ggctcgcaagaacctgatggatCACATGCAAgtgctcagggat (SEQ ID NO: 11) | 43 | 22 | 12 |
| 9 bp deletion | ggctcgcaagaacctgatggatg_____atcgccaggcgttctccg (SEQ ID NO: 12) | 41 | 23 | 18 |
| 3 bp change | GAGGCTCGCAAGAACCTGATGAGGGTGCTCAGGGATCGCCAGGC (SEQ ID NO: 13) | 44 | 21 | 20 |
| 3 bp change | CATGGTGCAAGTTGAACAACACCAAATGGTTTCCCGCGGAACC (SEQ ID NO: 14) | 43 | 20 | 20 |
| 3 bp change | CTATCCTGCAACATTTGGCCATACTAAACATGCTCCACCGTCG (SEQ ID NO: 15) | 43 | 20 | 20 |
| 3 bp change | CGAATCCGAAGGGAGAACGTATCTGCTGGTGAGCGTACGAAGC (SEQ ID NO: 16) | 43 | 20 | 20 |
| 3 bp change | AGCGAACGGGGCCAGGATATGTCTACTCTGGCATTTCTGGGGG (SEQ ID NO: 17) | 43 | 20 | 20 |

TABLE 1-continued

Mutagenic primers used for variant library and mutagenesis via SLUPT. Bold text indicates the mutated region. Single letter codes are used to denote base mixtures. N is the length of the primer, 5' is the number of bases on the 5' side of the mutation, 3' is the number of bases on the 3' side of the mutation.

| Donor primer name | 5'→3' donor primer sequences (all are 5' phosphorylated) | N | 5' | 3' |
|---|---|---|---|---|
| 3 bp change | ctccgagcgtacctggaaaactctcctgtccgttt (SEQ ID NO: 18) | 35 | 19 | 13 |
| 3 bp change | cgtacctggaaagtgctcctACGcgtttgccggacgtgggcgg (SEQ ID NO: 19) | 43 | 20 | 20 |
| Antibody libraries | | | | |
| Primer 1 | catgtagagcttctcagtctSTTRRTagttatctggattggtacca (SEQ ID NO: 20) | 46 | 20 | 20 |
| primer 2 | ctcccaaactgctcatctacGSCgctTYTtcttttgcagagcggcgtgcc (SEQ ID NO: 21) | 49 | 20 | 20 |
| primer 3 | catactattgccagcagtacKRTtcaWCAcccTKKacttttgggcccggaacaaa (SEQ ID NO: 22) | 65 | 20 | 20 |
| primer 4 | gatttactttctcaagctatRSTatgcactgggttcgccaagc (SEQ ID NO: 23) | 43 | 20 | 20 |
| primer 5 | gaaagggcttggaatgggtgRCCKTCatcTSGtatgacggatccaacaaata (SEQ ID NO: 24) | 62 | 20 | 20 |
| primer 6 | cggtctactactgtgccaggRMTSSAcgcggcgcaaccctgtacta (SEQ ID NO: 25) | 46 | 20 | 20 |
| primer 7 | gcggcgcaaccctgtactatTRSTRTKRTSSCatggatgtttggggacaagg (SEQ ID NO: 26) | 52 | 20 | 20 |

Annealing, extension and ligation of the primers: Typically, donor primer:ssDNA ratios around 1000:1 work well. Lower ratios will also work, but as the primer:template ratio decreases there is an increased likelihood of skipping a primer and obtaining the template sequence instead of the desired variants. The amount of ssDNA template used depends in part on the previous UDG test. Typically, for the recombinase study, ssDNA template was used at a concentration of ~2.5 ng/μl or ~10 fmol/μl. In this step, annealing occurs at room temperature, which favors random annealing of the primer mixtures to the template. Typically, 10 μl annealing reactions are performed in PCR tubes. Each reaction contains 1 μl 10× Taq ligase buffer, 10 fmol ssDNA, 10 pmol of 5' PCR forward primer, 10 pmol of donor primer mixture, and water to 10 μl total. The annealing reactions are incubated at room temperature for 30 minutes. For the extension and ligation reaction, 1 μl of the annealed sample, 1 μl 10× Taq DNA ligase buffer, and dNTP mixture are combined for a final concentration of 100 μM, 2.5 units Taq DNA ligase (New England Biolabs, M0208S), 0.75 units Phusion®-U-Hotstart polymerase, and water to 10 μl. This reaction is incubated at 55° C. for 30 minutes.

Inactivation of the template strand: Each reaction is digested with UDG for 30 minutes at 37° C. For example, in a 10 μl UDG digestion reaction, 2.5 μl gap filled template, 1 μl 10× reaction buffer, 1 μl UDG, and water to 10 μl was used.

Amplify the single-stranded library or mutant via PCR: 2.5 μl UDG-digested sample was used as template in a 50 μl PCR reaction with forward and reverse primers. No special conditions are necessary. Using Phusion® High-Fidelity polymerase (New England Biolabs, M0530) (which does not tolerate dU in the template) further ensures that none of the template sequence remains in the double-stranded product, though this is not usually a problem. PCR clean-up is performed using Machery-Nagel kits.

A step by step protocol of the SLUPT method is available on the Benchling website (benchling.com).

Sanger sequencing of SLUPT PCR products: The sequence of all libraries and mutations were characterized by Sanger sequencing. DNA sequences and traces were analyzed using SnapGene software (from Insightful Science; available at www.snapgene.com).

Molecular graphics: Molecular graphics figures were prepared using PyMOL (The PyMOL Molecular Graphics System, Version 2.3.4, Schrodinger, LLC).

Cloning, transformation, and NGS analysis: 1 μg of PCR product library and 2 μg of empty pEVO plasmid (18) were separately digested in 15 μl reactions with BsrgI and Xba1 (both from New England Biolabs). After gel purification and cleanup using a Macherey-Nagel kit, the library was ligated into the vector in a 50 μl reaction containing 20 μl of plasmid (13 ng/μl), 15 μl of insert (22 ng/μl), 10 μl 5× ligase buffer, and 5 μl of T4 DNA ligase (Invitrogen, 15224041). For the transformation, the entire reaction was added to 1 ml of homemade rubidium chloride competent Top 10 cells. After a 1-hour incubation on ice, the cells were heat shocked for 90 seconds at 42° C. and then incubated on ice for 2 minutes. The cells were then grown at 37° C. for 1 hour before an aliquot was removed for plating on chloramphenicol and subsequent colony counting. The remaining cells were transferred to a 65 ml flask of LB and grown overnight in the presence of chloramphenicol before plasmid purification. The purified plasmids were digested with BsrgI and Xba1, and the SLUPT DNA library was gel purified. The DNA library was then fragmented by sonication and subjected to paired end 150 bp sequencing using an Illumina MiSeq instrument. The resulting reads were aligned to the parent sequence using Bowtie2 (bowtie-bio.sourceforge.net/bowtie2/index), and the resulting BAM file was visually inspected using IGV (software.broadinstitute.org). The statistics presented in Table 3 were calculated using a short python script that used the pysam pileup function (pysam.readthedocs.io/en/latest/index). The output of this script incudes the base position, the fraction of reads with each of the four bases, and the total number of reads contributing to the count at each position. The results showed that the error rate is larger at both ends of the PhiX control alignment and at the 5' end of the library alignment. These increased errors are likely a sequencing artifact. The average error rates and standard deviations on these error rates are reported without the 25 bases at the 5' end of the library and without 5 bases at either end of the PhiX genome, which was spiked into the library as an internal control.

anti-CTLA4 scFv Antibody SLUPT library generation: A plasmid containing the anti-CTLA4 scFv antibody was obtained from Addgene (#85436). A scFv fragment was generated by standard PCR for use as the template in this study. An anti-CTLA4 scFv library was then created as described above, using the mutagenic donor primers presented in FIG. 4 and Table 1.

MSCS python script: The MSCS script is available for download at academic.oup.com. This script is designed to help users select degenerate codon mixtures that encode a desired set of amino acids. Based on user input, the script generates a sorted list of the 3,375 possible codon mixtures that can be easily synthesized, wherein the mixed bases are at same concentrations. The script is written in python3, and it requires the biopython module. This module is freely available at biopython.org and can be installed on many Linux systems by issuing the command apt-get install python3-biopython. To run the script from the command line, type python3 MSCS.py. Users will be prompted for a list of amino acids they would like encoded and then a list of weights (−1.0 to 1.0) for each of these amino acids. Negative weights indicate that the user prefers to not see the respective amino acid near the top of the output. Users are also prompted for penalty parameters for missing amino acids, for encoded but not requested amino acids, and for stop codons. The default parameters generally work well, but users are encouraged to experiment with other values and see the effect these have on the sorted output. Base mixtures are indicated using the standard code: B=C/G/T, D=A/G/T, H=A/C/T, K=G/T, M=A/C, N=A/C/G/T, R=A/G, S=C/G, V=A/C/G, W=A/T, Y=C/T.

The pEVO plasmid used to amplify both the test library and the five-primer mutagenesis test is based on a pBAD plasmid sequence from Addgene.

Results

To illustrate the utility of the SLUPT method, the synthesis and sequencing of libraries involving two well-known protein engineering targets (i.e., Cre recombinase and a single-chain antibody against CTLA4) are described below. The SLUPT method, which is outlined in FIG. 1, relies on a single-stranded dU-containing template that is enzymatically inactivated before the final library is amplified. The single-stranded template is synthesized in a PCR reaction in which the primer for the top strand is phosphorylated and the primer for the bottom strand is not. An exonuclease is used to selectively degrade the top strand, leaving the bottom single-stranded template. Primers homologous to the 5' end of the template and to the internal regions of the sequence to be altered are then annealed to the template. After the primers are extended and ligated, the dU-containing template strand is inactivated, and the resulting single-stranded library is then made double-stranded and amplified by conventional PCR.

In practice the SLUPT protocol can be divided into two parts: template preparation and DNA synthesis. A single template preparation (steps 1 and 2 in FIG. 1) is sufficient for hundreds of subsequent library and/or mutagenesis reactions. The library is synthesized and selectively amplified in the second part of the procedure (steps 3-5 in FIG. 1). This part of the method can be completed in one afternoon.

Recombinase Library Generation

Figure 2:
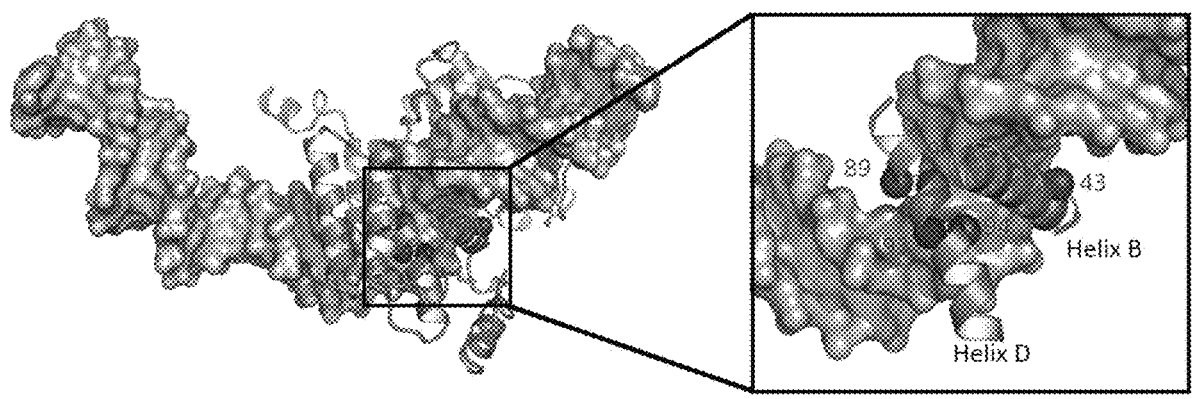
FIG. 2 shows a structure-based library design for a Cre-based recombinase. Left: A structural model of a Cre variant (cyan) bound to its target DNA (surface representation in grey) with only one monomer of the Cre tetramer shown. The location of the desired mutations is indicated by red spheres located at the C-alpha coordinates. Right: Close-up of the helix B (with amino acid 43) and helix D (with amino acids 89, 90, 93, and 94).

As an initial test and to illustrate the utility of this approach, a library of Cre recombinase variants with differences at amino acid positions 43, 89, 90, 93, and 94 was generated. These amino acids are in Helix B and Helix D of the enzyme, and both regions have been shown to interact with the DNA substrate in recombinase crystal structures (FIG. 2) (16). To limit the size of the library, only a subset of the 20 possible amino acids were included at each of the five amino acids positions that were varied. The primers used are shown in FIG. 3, and the amino acid changes are shown in Table 2.

TABLE 2

SLUPT library design for recombinase library 1.

| AA | Codon alteration[a] | Amino acid variants | AA frequency[b] | Rationale |
| --- | --- | --- | --- | --- |
| K43 | AAA > RRK | E, D, G, K, N, S, R | 1, 1, 2, 1, 1, 1, 1 | charged, polar, gly |
| L89 | CTG > VNA | A, E, G, I, K, L, Q, P, R, T, V | 1, 1, 1, 1, 1, 1, 1, 1, 2, 1, 1 | varied |
| Q90 | CAA > VNA | A, E, G, I, K, L, Q, P, R, T, V | 1, 1, 1, 1, 1, 1, 1, 1, 2, 1, 1 | varied |
| A93 | GCC > DSC | C, A, S, T, G | 1, 1, 2, 1, 1 | small, uncharged |
| Q94 | CAG > VDS | S, K, G, Q, D, V, I, R, H, M, L, E, N | 1, 1, 2, 1, 1, 2, 1, 3, 1, 1, 2, 1 | varied |

[a]Standard single letter codes for base mixtures are listed in this column. R = A/G, K = G/T, V = A/C/G, N = A/T/G/C, D = A/G/T, and S = G/C.
[b]The AA (amino acid) frequency refers to the number of times the amino acid in the variants list is represented by the given codon alteration, respectively.

A python script (discussed in greater detail below) was used to select the specific variants at each amino acid position that was modified. These choices resulted in a hypothetical, targeted library encoding 124,416 different codons and 55,055 different protein sequences. As noted in Table 2, some of the degenerate codon mixtures encoded certain amino acids more than once. This is difficult to avoid when using simple base mixtures but can be avoided if more complex primer mixtures are utilized (17).

The degree of variation in the SLUPT-generated library was visualized by Sanger sequencing. In theory, the synthetic oligonucleotides used to form the library should contain equal amounts of the two, three, or four bases that were selected at each varied position. As shown by the chromatographic sequencing traces in FIGS. 3A and 3B, the amounts of the four bases are in general agreement with the expected values. SLUPT can also be used to make simple base substitutions, as is the case at the position marked with a red arrow in FIG. 3B, where guanosine is mutated to adenosine. The efficiency of the approach is highlighted by the absence of alternative bases at this position. Importantly, the starting sequence is not preferred, as might be expected if the U-containing template was not completely deactivated or if oligonucleotides with greater base complementarity selectively hybridized to the template.

Interestingly, the roughly equal distribution of bases at the selected, degenerate positions is much less evident if an initial 95° C. denaturing step is performed when the donor primers are first added to the template. Inclusion of this heating step favors annealing of oligonucleotides that are most homologous to the starting sequence. This unequal distribution of bases is particularly evident when mutating a G/C base pair adjacent to another G/C pair that is not mutated (blue triangles in FIG. 3C). Most likely, the heating facilitates free exchange and competition between primers while the sample cools. This pattern is highly reproducible, and the variation appears to result from differences in the stability of different partially duplex structures. While the denaturing step in the annealing process should generally be avoided when making libraries, the reproducibility of the effect suggests that it may be useful in evaluating the relative energies of various mismatched duplex structures. It is notable that the absence of a denaturation step prior to primer annealing further differentiates SLUPT from other methods that involve PCR with mutagenic primers, such as multisite QuikChange®, megaprimer extension, and gene assembly schemes.

Figure 5:
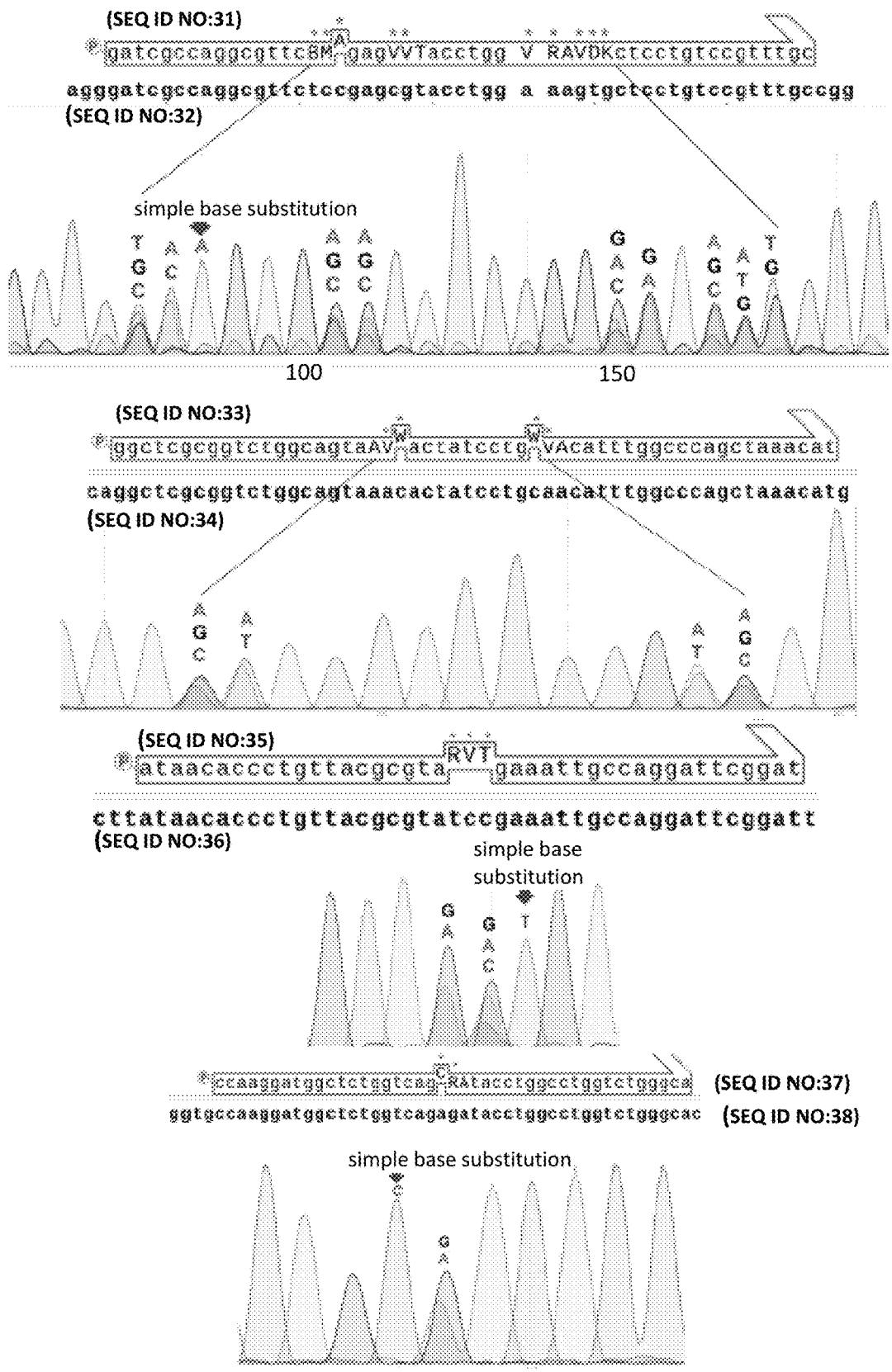
FIG. 5 shows Sanger sequencing results from a recombinase library that was generated using four mutagenic donor primers. In each case, the 5' phosphorylated donor primer (purple box) is shown aligned the starting sequence (lowercase bold). Below is the interpreted sequence and the Sanger sequencing trace. This same library was also subjected to NextGen sequencing.

To better understand the diversity and quality of libraries synthesized via SLUPT, and to help evaluate the degree of library diversity after the SLUPT PCR product libraries are cloned into a plasmid and transformed into cells, a second Cre recombinase-based library wherein 19 selected base pairs in four distinct regions were simultaneously altered was synthesized. One mutagenic primer was used for each of the four altered regions (FIG. 5). To help evaluate the diversity of this library in bacterial cells, the library was cloned into a plasmid and transformed into E. coli, yielding approximately 900,000 colony forming units. The plasmids were then extracted from an overnight bacterial culture, and the library was cut out of the plasmids and gel purified. The DNA encoding the Cre variant library was fragmented by sonication and subjected to paired-end Next Generation Sequencing (NGS). The same sample was submitted for Sanger sequencing and the resulting sequencing chromatograms are presented in FIG. 5. Although the Sanger chromatograms are a far less accurate measure of variable base incorporation and background, general agreement between the Sanger sequencing and the NGS results was found. This validates the use of Sanger traces to estimate the quality of a library.

NGS resulted in 846,322 DNA reads, of which over 97% aligned to the Cre-based index sequence using default settings in the program Bowtie2. Both the Sanger sequencing chromatograms and NGS counts show that the expected mutations and variations were very well-represented in the library extracted from the cells. NGS resulted in at least 56,000 reads for each position within the sequence, and the fraction of each nucleotide in the mutated regions is presented in Table 3. In cases where a simple mutation was encoded, the expected mutation was present in ~99% of the reads. When two bases were encoded, ratio pairs ranged from 62%:38% to 50%:49%. When three bases were encoded, ratio triplets ranged from 52%:29%:19% to 37%:34%:29%.

TABLE 3

Summary of NGS results at the altered nucleotide positions. For each of the four altered regions, the first column indicates the nucleotide position and nature of the mutation, and the second column summarizes the NGS results. Bases in lowercase were not encoded by the mutagenic primers and were not expected in the library. Bases in bold were encoded by the template.

| Region 1 | | Region 2 | | Region 3 | | Region 4 | |
|---|---|---|---|---|---|---|---|
| 112 T > B | T 44%, G 33%, C 23%, a 0.1% | 257 A > V | G 40%, A 34%, C 26%, t 0.1% | 523 T > R | G 63%, A 36%, t 0.4%, c 0.0% | 844 A > C | C 99%, A 0.7%, t 0.1%, g 0.0% |
| 113 C > M | A 58%, C 42%, g 0.1%, t 0.0% | 258 G > W | T 51%, A 48%, g 0.1%, c 0.1% | 524 C > V | G 43%, C 29%, A 27%, t 0.1% | 845 G > R | G 59%, A 41%, c 0.1%, t 0.0% |
| 114 C > A | A 99%, C 1.1%, g 0.1%, t 0.0% | 268 C > W | A 50%, T 49%, c 0.1%, g 0.1% | 525 C > T | T 99%, C 0.5%, g 0.1%, a 0.1% | | |
| 118 C > V | A 37%, G 34%, C 29%, t 0.0% | 269 A > V | G 41%, A 39%, C 19%, t 0.1% | | | | |
| 119 G > V | G 43%, A 29%, C 27%, t 0.1% | | | | | | |
| 127 A > V | G 42%, A 37%, C 20%, t 0.1% | | | | | | |
| 128 A > R | A 53%, G 47%, T 0.1%, c 0.0% | | | | | | |
| 130 G > V | G 52%, A 29%, C 19%, t 0.1% | | | | | | |
| 131 T > D | T 46%, A 28%, G 26%, c 0.1% | | | | | | |
| 132 G > K | G 62%, T 38%, a 0.1%, c 0.1% | | | | | | |

Outside of the mutated nucleotides, the average frequency of unexpected bases is 0.209% (SD=0.093% with an average of 210,113 reads at each position). Most of these changes are single base substitutions. The frequency of these random errors is similar within and outside of the regions covered by the mutagenic primers. For instance, the average error rate for bases within three nucleotides of a mutated base is 0.188% (SD=0.074%). An internal PhiX control sequence with a different barcode was spiked into the library before sequencing. The average per-base error rate in the PhiX control was 0.106% (SD=0.134% with an average of 2,018 reads at each position). Thus, errors are about 0.1% more common in the library than in the control.

Little bias from the starting sequence was found at positions where the template encoded one of the bases included in that site's base mixture. The template-encoded base was most highly represented in 46% of such cases (6 mutated positions out of 13). The fraction expected by chance is 37% (4 positions encoded 2 bases, and 9 positions encoded 3 bases in this particular library). Thus, the 13 data points indicate a weak preference for mutagenic oligonucleotides that are more complementary to the template. Still, this preference seems to be minor, and since the precise base ratios in the mutagenic primers is not known, it is difficult to draw any quantitative conclusions. Importantly, the observed ratios indicate very strong representation of all encoded nucleotides and will be sufficient for most applications.

Very low levels of template sequence were also observed at positions where the template base was not included in the mutagenic primers (0.1-1.1%). Since such templated-base errors are not uniform across all sites, these imperfections in the library are unlikely to arise from a failure to fully degrade the template before library amplification. It is most likely that these errors arise when one of the mutagenic primers fails to anneal to the template during the elongation/ligation step. Again, it is expected that such errors will be acceptable for most applications. Moreover, these data demonstrate that SLUPT yields significantly lower background from the starting sequence than some alternative methods.

Figure 6:
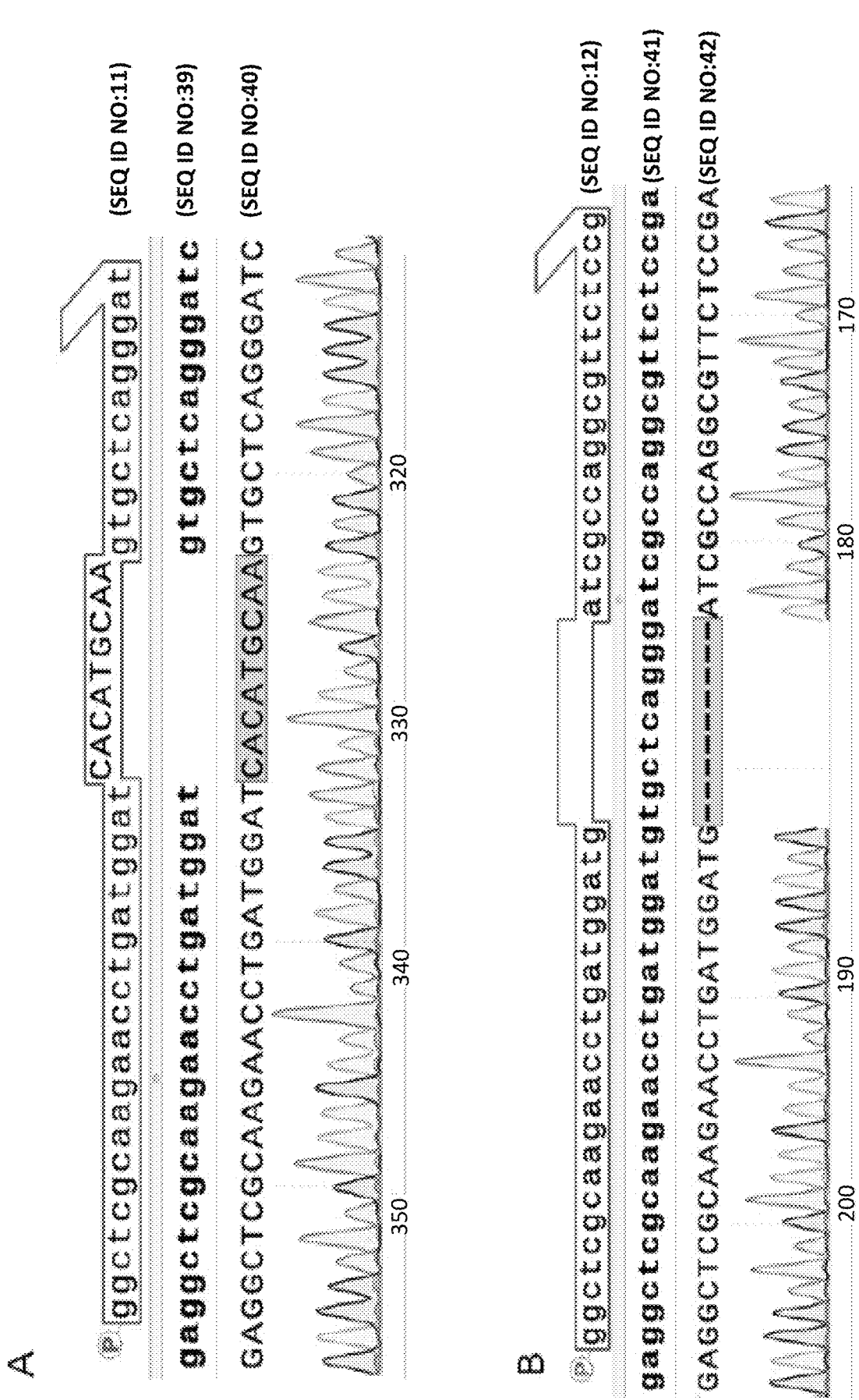
FIG. 6 shows Sanger sequencing results for recombinase mutants containing a nine base pair insertion (A) or deletion (B) that were created using the SLUPT method. The 5' phosphorylated donor primer (purple box) is shown aligned the starting sequence (lowercase bold). Below the starting sequence is the interpreted sequence and the Sanger sequencing trace. These traces demonstrate that the mutagenesis has been successful in a large majority of DNA molecules.

The high frequency of primer incorporation described above suggests that SLUPT may be useful for multisite mutagenesis applications. To validate the utility of SLUPT for this purpose, a series of simple mutations that included insertions, deletions, and substitutions was synthesized. Primers used for the recombinase SLUPT studies are shown in Table 1. As a more challenging test, SLUPT was then used to create a nine base pair deletion and a nine base pair insertion. In each case, the resulting mutants had no obvious background from the starting sequence (FIG. 6). To test the ability to make multiple three base pair changes across the gene, SLUPT was used to make five mutations simultaneously using five donor primers spaced 50 base pairs apart. The five donor primers are shown aligned to the template sequence in FIG. 7. After confirming the expected mutations by Sanger sequencing of the SLUPT PCR product, the DNA was cloned into a plasmid and transformed into E. coli as above. Six single colonies were sequenced in both directions. Consistent with the high rate of primer incorporation seen in the NGS experiment, all six colonies contained all five mutations. Consistent with the error rate described above, three of the six clones had point mutations outside of the mutated bases. One of these mutations, a single nucleotide deletion, was in a region covered by the mutagenic primers, but outside of the region that was mutated. The other two mutations were base substitutions that occurred in regions between primers.

It was next determined whether the spacing between the donor primers was a factor in the efficiency of the mutated products, and it was found that it was not. Primers cannot overlap, but they can be very close to one another. The closest donor primer sets tested to date were 2 bp apart, and the farthest donor primer sets tested were 440 bp apart (data not shown). Libraries with more than six donor primers have not yet been synthesized via SLUPT, but previous work with single-stranded DNA templates has shown that as many as 10 primers can be used in simultaneous mutagenesis reactions (18). Provided that the primers do not hybridize to each other, these results indicate that using additional donor primers in reactions with PCR-derived dU-containing templates is not problematic.

Antibody Library Generation

Next, it was tested whether SLUPT would be well-suited for antibody engineering, and particularly for construction and optimization of single chain antibody (scFv) molecules. These molecules have a variety of uses in the laboratory and clinic (19, 20). scFvs can be developed ab initio, by screening libraries with randomized antibody fragments (21), or they can be constructed by splicing together sequences from the Fv heavy and Fv light chains of intact antibodies with the desired specificity (22, 23). In all cases, a protein linker (typically 15-20 amino acids long) is used to connect the two immunoglobulin domains. Strategies for generating site-directed scFv libraries usually rely on primer extension, gene assembly, recombination, or single-stranded templates to generate the necessary genetic diversity (14, 22, 24, 25).

SLUPT allows for selective targeting of residues in the paratope that have been determined to be important to epitope binding based on structural and/or interaction studies of the antibody and ligand. To test SLUPT in the context of scFv library construction, an antibody against cytotoxic T-lymphocyte-associated protein 4 (CTLA-4) was used. CTLA-4 is an immune checkpoint molecule that is involved in down-regulation of the T-cell-mediated immune response (26, 27). Two monoclonal CTLA-4 antibodies have been developed and undergone clinical testing: Ipilimumab has been effective in the treatment of melanoma (28), and Tremelimumab has been used in multiple phase III clinical trials (29, 30). Crystal structures of both an scFv version of Ipilimumab and the Fab fragment of Tremelimumab have been determined in complex with CTLA-4. These structures revealed that Tremelimumab and Ipilimumab target the same epitope of CTLA-4 and have very similar structures (31, 32).

Figure 4A:
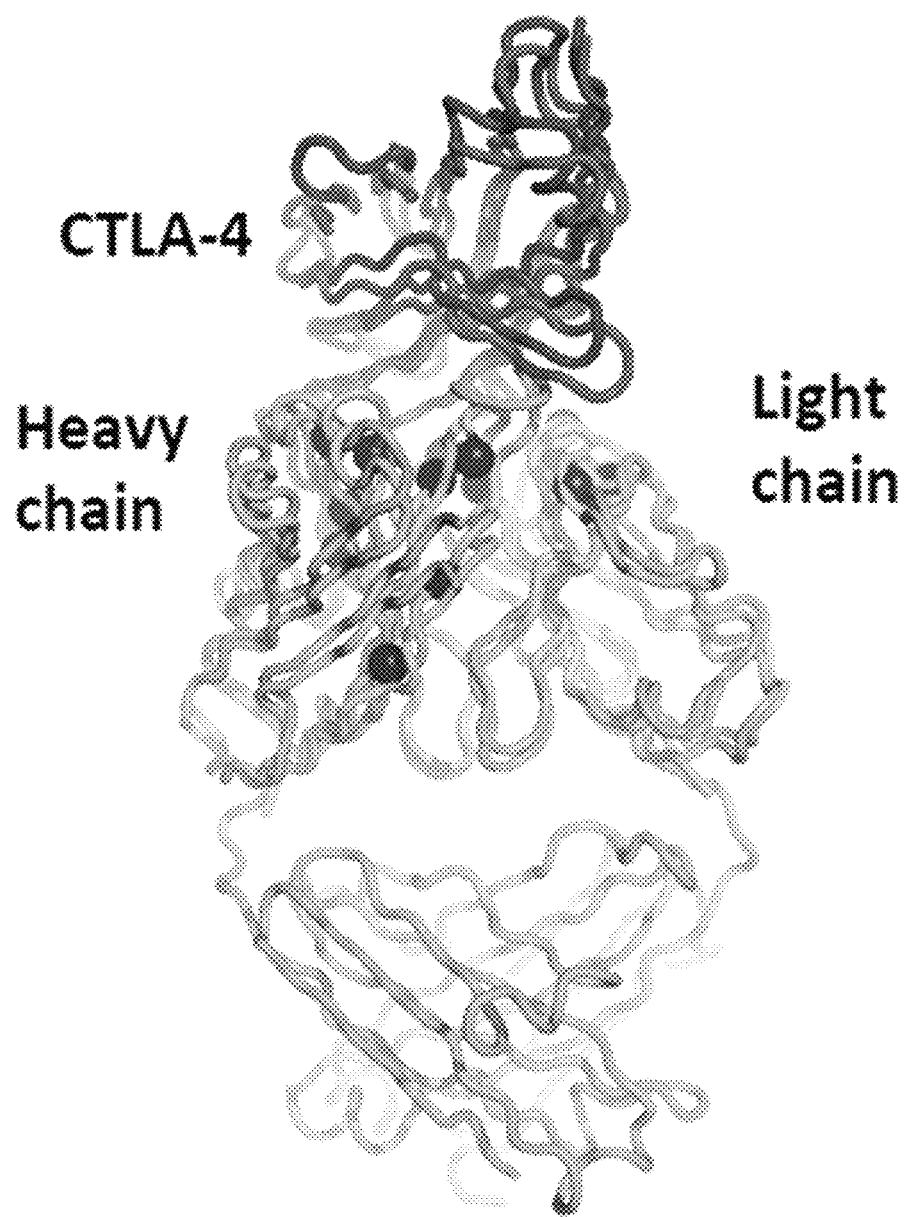
FIG. 4 shows a structure-based library design for an anti-CTLA-4 scFv antibody. (A) Superimposed crystal structures of the scFv ipilimumab (green, pdb code 5XJ3) and the Fab fragment of tremelimumab (teal, pdb code 5GGV). CTLA-4, seen in both structures, is magenta and red, respectively. The locations of the mutated residues within the library are shown as blue spheres. (B) SLUPT donor primers used to create the DNA libraries of the scFv gene in a single reaction. The donor primers are in a purple box aligned to the wild-type scFv sequence. The overlapping primers were not used together, and there are six donor primers per library. The primers span ~650 nucleotides, the closest pair is 5 bp. The farthest pair is ~130 bp. The scFv PCR product is ~900 base pairs.
Figure 4B:
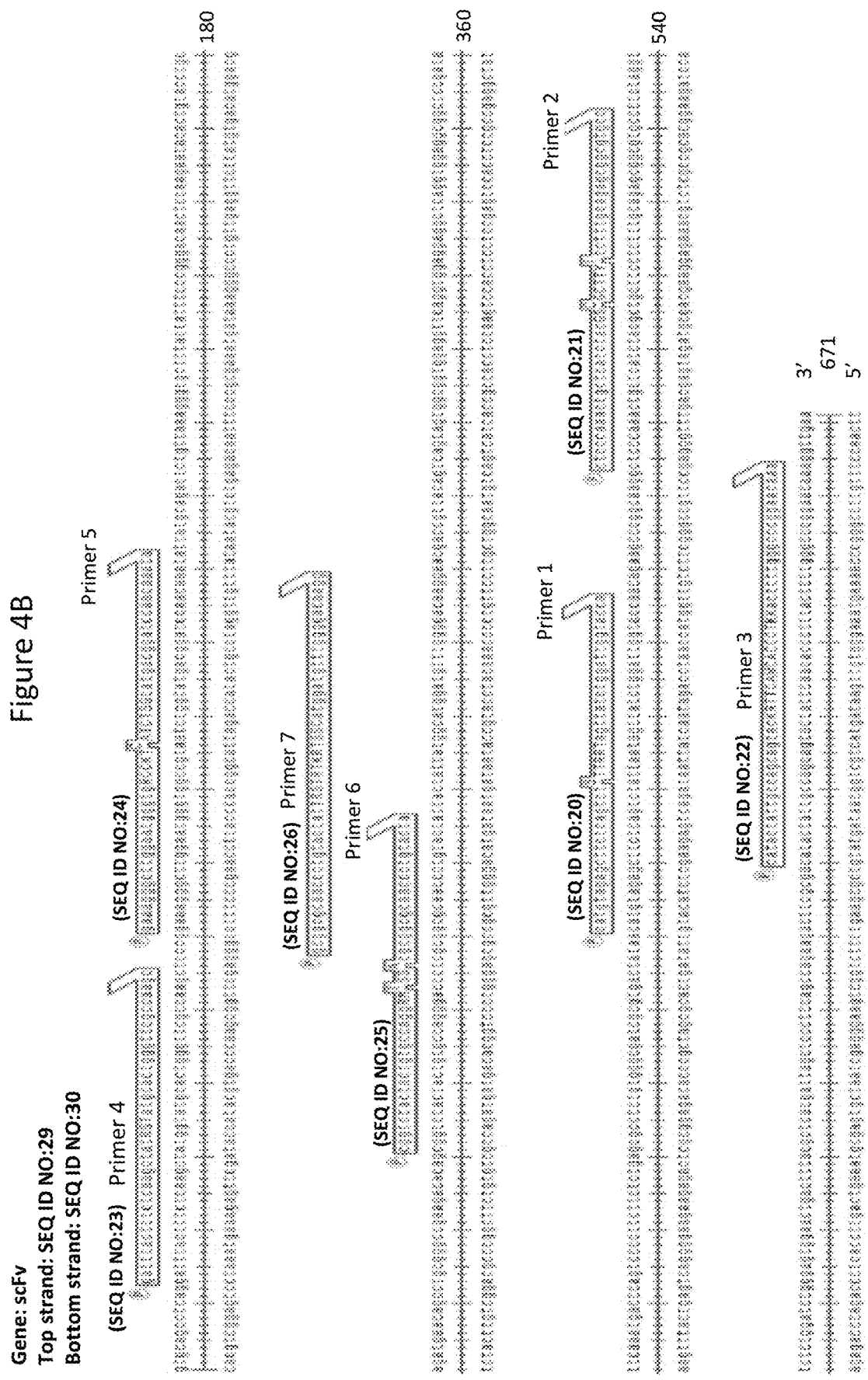

To demonstrate how SLUPT might be used in a situation like this, the two structures were examined and residues that both interact with CTLA-4 and differ in the antibody sequences were identified Then, a library consisting of a mixture of these residues was generated (FIG. 4). The library was designed using Tremelimumab as the starting gene. The seven light-chain residue positions and ten heavy chain positions that were mutated are detailed in Table 4. The primers used to make these mutations and the base mixtures at the mutated positions are listed in FIG. 8. In some instances, the genetic code made it impossible to encode only the two desired amino acids (capitalized letters in Table 4), and two other codons were also encoded (lowercase letters in Table 4). To avoid having to use a very long primer, libraries were generated with either primer 6 or primer 7. It was necessary to create two separate libraries due to the overlapping nature of these primers.

TABLE 4

SLUPT Library design for anti-CTLA-4 scFv studies.

| Primer | Chain | Amino acid variants[a] |
|---|---|---|
| 1 | Light | position 29: L/V, position 30: N/G/s/d |
| 2 | Light | position 50: A/G, position 52: S/F |
| 3 | Light | position 92: Y/G/c/d, position 94: T/S, position 96: F/W/c/l |
| 4 | Heavy | position 33: G/T/a/s |
| 5 | Heavy | position 49: A/T, position 50: V/F, position 52: W/S |
| 6 | Heavy | position 99: D/T/a/n, position 100: P/G/r/a |
| 7 | Heavy | position 108: Y/W/c/*, position 109: Y/C, position 110: Y/G/c/d, position 111: G/P/r/a |

[a]Amino acid residues present in the two antibodies are shown in capital letters, additional mutations encoded by the base mixtures chosen are shown in lowercase. The asterisk in primer 7 denotes an encoded stop codon.

Figure 8:
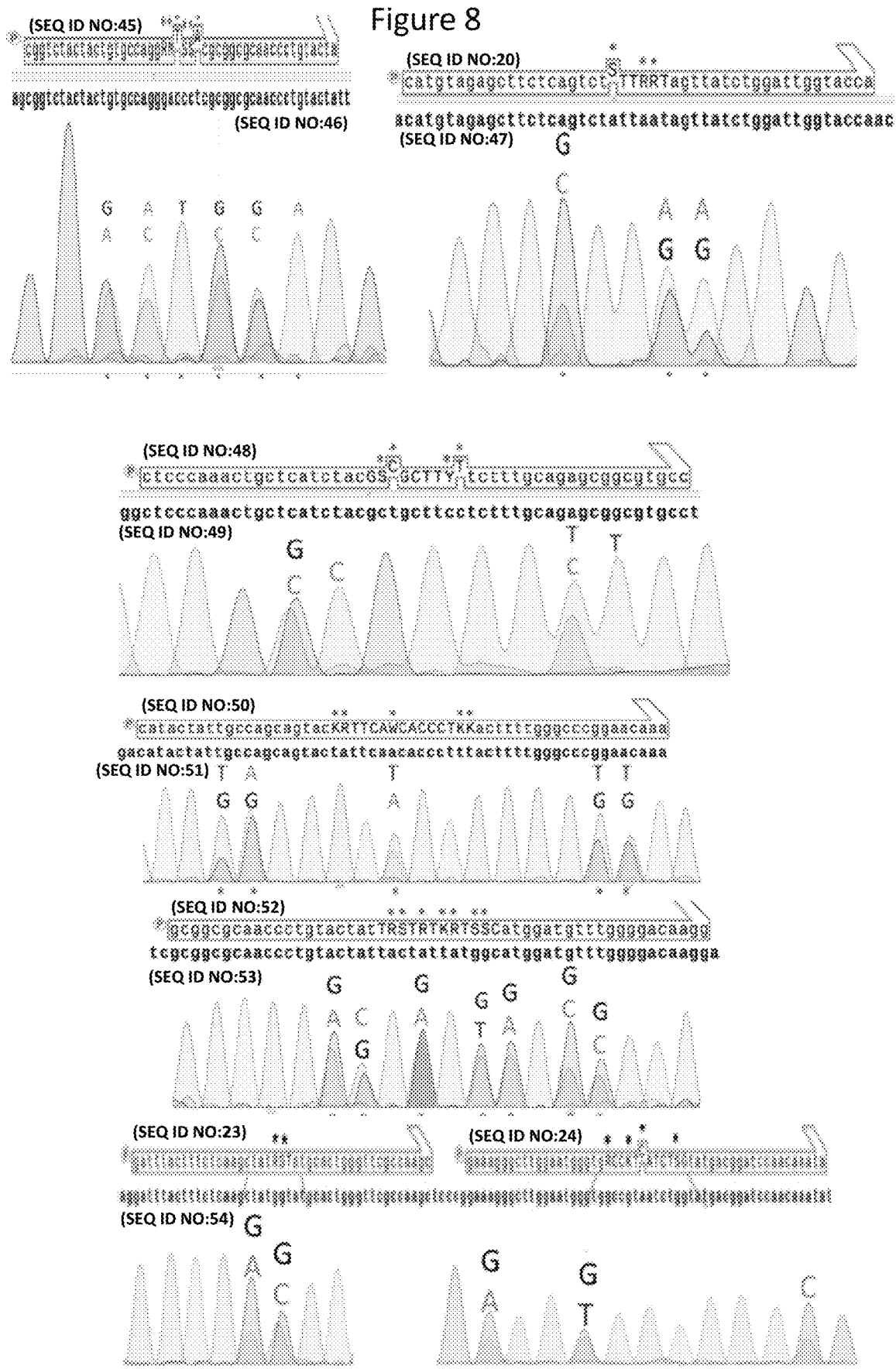
FIG. 8 shows Sanger sequencing results for seven mutated anti CTL-4 antibody regions. The donor primers (outlined in purple box) are shown aligned to the scFv template. Altered bases are indicated by a *.

In both cases, as with the earlier Cre recombinase libraries, Sanger sequencing was used to confirm the presence of the various nucleotides in the libraries (FIG. 8). The results were similar to those discussed above, with no obvious bias towards the starting sequence and good representation of all alternative bases at the selected sites of genetic variation.

A Program to Assist in Degenerate Codon Selection

To maximize the utility of SLUPT, it is important to optimize the base choices at each varied position within the synthesized libraries. A number of clever base mixtures for use in library creation have been described. The goal of these mixtures is to maximize the number of amino acids at each varied position while minimizing the redundancies that are intrinsic to the genetic code. For instance, the 'small intelligent' approach uses four mixtures to encode each of the 20 amino acids just once (33), and the NDT approach encodes just 12 chemically varied amino acids just once within a single mixture (34). Another productive approach has limited the size of DNA libraries by sampling only amino acids that are seen in sequence alignments of homologous proteins or based on 3D structures. In these cases, the optimal base mixtures can be chosen by entering the desired amino acids into programs such as MDC Analyzer (17, 35).

To keep things relatively simple and cost-effective, particularly in cases where a variety of amino acids are being varied via a single donor primer, the complete set of possible codon mixtures that can be synthesized using a conventional DNA synthesizer was considered. At each of the three positions within a codon, one can have 15 possibilities (1 mixture of all four bases, 4 mixtures with one base missing, 6 mixtures of two bases, and 4 individual bases). Thus, there are $15^3 = 3,375$ possible choices for each codon. To assist users in selecting the most appropriate codon mixture, a python script named MSCS (Mixed Synthesis Codon Selector) has been written. This software tool takes as input the desired list of amino acids that one wishes to encode and a series of weights (values between −1 and 1) that describe how important each amino acid is to the user. Negative weights are used in cases where one wishes to reduce the likelihood of seeing the specified amino acid near the top of the output list of suggested codons. Users can also input parameters that reduce the likelihood of seeing mixtures containing stop codons, mixtures that encode extra amino acids, and mixtures where requested amino acids are missing. Using this information, an ordered list of potential codon mixtures that best satisfies the request is presented to the user.

For instance, with default parameters, inputting the amino acid list A, T, F, W, and C with weights 1.0, 1.0, 0.5, 1.0, and 0.2 yields the exemplary output shown below (note: only the top of the list is shown). Each line of the output is a codon mixture, and the bases within this mixture are described by the last three characters. The program uses a standard nomenclature for base mixtures (see Methods). The top line of the output indicates that a codon with A/G/T in the first position, G/C in the second position, and G in the third position encodes each of the most desired amino acids one time, but does not encode F or C which were also requested but weighted less highly. Although they were not requested, this mixture also encodes R, S, and G. Looking down the list, one sees two solutions (in bold) where all five of the requested amino acids are encoded, but not with the same frequency, and with seven unrequested amino acids also in the mix. As demonstrated here, there is not always one obviously best codon mixture. Even in these cases, however, this tool will be helpful in making informed choices as one designs a DNA library.

Exemplary Output of the Mixed Synthesis Codon Selector Python Script

```
3/5 Encoded: A1 T1 W1 Missing: F C Extra: S1 G1 R1 Codons: 6 Code: dsg
2/5 Encoded: T1 A1 Missing: F C W Extra: 0 Codons: 2 Code: rca
2/5 Encoded: T1 A1 Missing: F C W Extra: 0 Codons: 2 Code: rot
2/5 Encoded: T1 A1 Missing: F C W Extra: 0 Codons: 2 Code: rcg
2/5 Encoded: T1 A1 Missing: F C W Extra: 0 Codons: 2 Code: rcc
3/5 Encoded: A1 T1 F1 Missing: C W Extra: S1 V1 I1 Codons: 6 Code: dyt
3/5 Encoded: A1 T1 F1 Missing: C W Extra: S1 V1 I1 Codons: 6 Code: dyc
2/5 Encoded: T1 A1 Missing: F C W Extra: S1 Codons: 3 Code: dca
2/5 Encoded: T1 A1 Missing: F C W Extra: S1 Codons: 3 Code: dct
2/5 Encoded: T1 A1 Missing: F C W Extra: S1 Codons: 3 Code: dcg
2/5 Encoded: T1 A1 Missing: F C W Extra: S1 Codons: 3 Code: dcc
2/5 Encoded: T1 A1 Missing: F C W Extra: P1 Codons: 3 Code: vca
2/5 Encoded: T1 A1 Missing: F C W Extra: P1 Codons: 3 Code: vct
2/5 Encoded: T1 A1 Missing: F C W Extra: P1 Codons: 3 Code: vcg
2/5 Encoded: T1 A1 Missing: F C W Extra: P1 Codons: 3 Code: vcc
3/5 Encoded: A1 T1 W1 Missing: F C Extra: S1 G1 R2 P1 Codons: 8 Code: nsg
5/5 Encoded: A2 T2 F1 W1 C1 Missing: 0 Extra: L1 S3 V2 G2 R1 I1 M1 Codons: 18
Code: dbk
5/5 Encoded: A2 T2 F1 W1 C1 Missing: 0 Extra: L1 S3 V2 G2 R1 I1 M1 Codons: 18
Code: dbs
4/5 Encoded: A2 T2 W1 C1 Missing: F Extra: S3 G2 R1 Codons: 12 Code: dsk
4/5 Encoded: A2 T2 W1 C1 Missing: F Extra: S3 G2 R1 Codons: 12 Code: dss
2/5 Encoded: T1 A1 Missing: F C W Extra: I1 V1 Codons: 4 Code: rya
2/5 Encoded: T1 A1 Missing: F C W Extra: I1 V1 Codons: 4 Code: ryt
```

DISCUSSION AND CONCLUSIONS

Prior methods for multiple site mutagenesis were limited in usefulness or cumbersome, requiring special strains of bacteria, phage infection, and phage DNA isolation prior to library synthesis, would not work with synthetic donor primers because the 5' exonuclease activity of the polymerase used degrades the primers or did not involve degradation of the nontemplate strand or inactivation of the template after the product strand has been synthesized. Thus, relative to earlier methods, SLUPT simplifies the process of generating the template, eliminates the heating step prior to primer annealing (likely leading to more uniform sampling), and utilizes a high-fidelity polymerase that is compatible with both dU bases and relatively short mutagenic primers.

Many protein engineering projects proceed in two phases. Initially, targeted mutations may be made in rationally chosen regions (e.g., CDR loops of antibodies or regions near the active site of an enzyme). Once the desired activity has been detected, random mutagenesis is often used as a second step to identify changes that optimize properties such as solubility, stability, binding, and/or enzymatic activity. The comparatively uniform sampling of mutations in selected regions makes SLUPT ideally suited for the initial screening phase of the protein engineering workflow. In view of the speed and minimal cost associated with the synthesis of subsequent libraries, along with the ease with which random mutations can be incorporated alongside the targeted changes (i.e., using error-prone PCR in the final amplification step), SLUPT will facilitate improvements to protein engineering workflows. For example, a large series of different libraries, each with diversity in multiple, different noncontiguous protein domains, may be screened to narrow down the regions that are important for altered function. SLUPT can be used for the synthesis of second-generation libraries with expanded diversity in key regions. The results can be used to refine diversity in key regions while random mutations are introduced (14).

SLUPT is particularly well suited for situations where rapid, inexpensive synthesis of a series of libraries or mutations is beneficial. Thus, SLUPT will find application in a broad array of directed evolution, mutagenesis, and protein engineering efforts. It will allow users to better use sequence alignments and structural information to enhance the rate at which desirable mutations are uncovered. The speed, efficiency, low cost, and robustness of this approach, along with the stoichiometrically balanced nature of the product libraries, make SLUPT well-suited for many applications.

Primer Skipping

As discussed in the main text, templated bases were occasionally seen in cases where the templated base was not encoded by the library. NGS of the second Cre-based library indicates that this occurred 1.1% of the time for primer 1, 0.1% of the time for primer 2, ~0.5% of the time for primer 3, and 0.7% of the time for primer 4 (see Table 3). If these values were uniform across the four regions, one might conclude that they are the result of undigested template. However, since they are not uniform, the most likely explanation is that mutagenic primers are occasionally skipped during the SLUPT extension/ligation step. Accordant with this idea, the occurrence of templated bases appears to be consistent within primers. Positions 258 and 268 (both encoded by primer 2) both show a 0.1% fraction of the template, and positions 523 and 525 (both encoded by primer 3) both show a ~0.5% fraction of the template. Primers 1 and 4 had only 1 position each (114 and 844, respectively) where the templated base was not encoded by the degenerate primers. The Tm values (neglecting the mutated bases) of the four mutagenic primers are 71, 70.5, 66, and 72, respectively. Thus, there does not appear to be a strong correlation between melting temperature and the frequency of "primer skipping". The particular library that was submitted for NGS was created using a primer:template ratio of 500:1. SLUPT mutations and libraries using a variety of primer:template ratios (1:100-1:10,000) have been generated. In most applications, a small fraction of templated sequence will not be a problem. Furthermore, increasing the ratio of primers to template should reduce the background even further in cases where this is critical.

Mutagenesis Efficiency

NGS demonstrates that SLUPT was at least 98.9% efficient for single-site mutagenesis and approximately 97.6% efficient for four sites. These values are based on the observed frequency of the templated base at positions where the primers do not encode this nucleotide (discussed above). Based on these positions, the efficiencies for the four primers are estimated to be 98.8%, 99.9%, 99.5%, and 99.3%, respectively. (The product of these yields 97.6%, the efficiency of getting all four mutations.) This estimate is consistent with the mutagenesis experiment in which five regions were simultaneously altered in a single reaction (FIG. 7), the results of which showed that six out of six sequenced clones had all five regions mutated.

Random Errors

As is noted in the main text, both the NGS results and the sequencing of individual clones generated via SLUPT showed approximately one random error per 1,000 base pairs. These errors do not seem to involve any particular bases, nor do they seem to be more common in some parts of the gene than others. For instance, they are not much more common near the ends of mutagenic primers or close to bases that have been mutated than they are in the regions between the primers. Based on this distribution, these random errors may arise during the final PCR amplification step. As a result, purifying the ssDNA from the mixture of mutagenic primers, degraded template, and inactivated enzymes before amplification might increase fidelity. In many multisite mutagenesis applications, this shortcoming may be mitigated by sequencing multiple clones.

REFERENCES

1. A. V. Shivange, J. Marienhagen, H. Mundhada, A. Schenk and U. Schwaneberg, Advances in generating functional diversity for directed protein evolution, *Curr Opin Chem Biol* 13 (2009) 19-25.
2. J. F. Chaparro-Riggers, K. M. Polizzi and A. S. Bommarius, Better library design: data-driven protein engineering, *Biotechnol J* 2 (2007) 180-191.
3. J. Bendl, J. Stourac, E. Sebestova, O. Vavra, M. Musil, J. Brezovsky and J. Damborsky, HotSpot Wizard 2.0: automated design of site-specific mutations and smart libraries in protein engineering, *Nucleic Acids Res.* 44 (2016) W479-487.;
4. M. Musil, J. Stourac, J. Bendl, J. Brezovsky, Z. Prokop, J. Zendulka, T. Martinek, D. Bednar and J. Damborsky, FireProt: web server for automated design of thermostable proteins, *Nucleic Acids Res.* 45 (2017) W393-W399.
5. P. Panigrahi, M. Sule, A. Ghanate, S. Ramasamy and C. G. Suresh, Engineering Proteins for Thermostability with iRDP Web Server, *PLoS ONE* 10 (2015) e0139486.
6. L. Sumbalova, J. Stourac, T. Martinek, D. Bednar and J. Damborsky, HotSpot Wizard 3.0: web server for automated design of mutations and smart libraries based on sequence input information, *Nucleic Acids Res.* 46 (2018) W356-W362.
7. W. M. Barnes and E. R. Frawley, Streamlined gene assembly PCR, CSHProtoc 2008 (2008), doi:10.1 101/ pdb.prot4862.
8. C. G. Acevedo-Rocha and M. T. Reetz, Assembly of Designed Oligonucleotides: a useful tool in synthetic biology for creating high-quality combinatorial DNA libraries, *Methods Mol. Biol.* 1179 (2014) 189-206.
9. F. Zeng, J. Zang, S. Zhang, Z. Hao, J. Dong and Y. Lin, AFEAP cloning: a precise and efficient method for large DNA sequence assembly, *BMC Biotechnol.* 17 (2017) 81.
10. F. Zeng, S. Zhang, Z. Hao, S. Duan, Y. Meng, P. Li, J. Dong and Y. Lin, Efficient strategy for introducing large and multiple changes in plasmid DNA, *Sci Rep* 8 (2018) 1714.
11. D. G. Gibson, L. Young, R.-Y. Chuang, J. C. Venter, C. A. Hutchison and H. O. Smith, Enzymatic assembly of DNA molecules up to several hundred kilobases, *Nat. Methods* 6 (2009) 343-345.
12. A. Hidalgo, A. Schließmann and U. T. Bornscheuer, One-pot Simple methodology for CAssette Randomization and Recombination for focused directed evolution (OSCARR), *Methods Mol. Biol.* 1179 (2014) 207-212.
13. K. M. Goh, K. J. Liew, K. P. Chai and R. M. Illias, Use of Megaprimer and Overlapping Extension PCR (OE-PCR) to Mutagenize and Enhance Cyclodextrin Glucosyltransferase (CGTase) Function, *Methods Mol. Biol.* 1498 (2017) 385-396.
14. D. Caucheteur, G. Robin, V. Parez and P. Martineau, Construction of Synthetic Antibody Libraries, *Methods Mol. Biol.* 1827 (2018) 93-108.
15. T. A. Kunkel, Rapid and efficient site-specific mutagenesis without phenotypic selection, *Proc. Natl. Acad. Sci. U.S.A.* 82 (1985) 488-492.
16. F. Guo, D. N. Gopaul and G. D. van Duyne, Structure of Cre recombinase complexed with DNA in a site-specific recombination synapse, *Nature* 389 (1997) 40-46.
17. L. Tang, X. Wang, B. Ru, H. Sun, J. Huang and H. Gao, MDC-Analyzer: a novel degenerate primer design tool for the construction of intelligent mutagenesis libraries with contiguous sites, *BioTechniques* 56 (2014) 301-302.
18. A. Seyfang and J. H. Jin, Multiple site-directed mutagenesis of more than 10 sites simultaneously and in a single round, *Anal. Biochem* 324 (2004) 285-291.
19. S. Krah, C. Schroter, S. Zielonka, M. Empting, B. Valldorf and H. Kolmar, Single-domain antibodies for biomedical applications, *Immunopharmacol Immunotoxicol* 38 (2016) 21-28.
20. W. R. Strohl, Current progress in innovative engineered antibodies, *Protein Cell* 9 (2018) 86-120.
21. T. Clackson, H. R. Hoogenboom, A. D. Griffiths and G. Winter, Making antibody fragments using phage display libraries, *Nature* 352 (1991) 624-628.
22. J. Andris-Widhopf, P. Steinberger, R. Fuller, C. Rader and C. F. Barbas, Generation of human Fab antibody libraries: PCR amplification and assembly of light- and heavy-chain coding sequences, *Cold Spring Harb Protoc* 2011 (2011), doi:10.1 101/pdb.prot065565.
23. J. S. Huston, D. Levinson, M. Mudgett-Hunter, M. S. Tai, J. Novotny, M. N. Margolies, R. J. Ridge, R. E. Bruccoleri, E. Haber and R. Crea, Protein engineering of antibody binding sites: recovery of specific activity in an anti-digoxin single-chain Fv analogue produced in *Escherichia coli, Proc Natl Acad Sci USA* 85 (1988) 5879-5883.
24. J. Y. Lai, Q. Loh, Y. S. Choong and T. S. Lim, Cassette hybridization for vector assembly application in antibody chain shuffling, *BioTechniques* 65 (2018) 269-274.
25. D. Sblattero and A. Bradbury, Exploiting recombination in single bacteria to make large phage antibody libraries, *Nature Biotechnology* 18 (2000) 75-80.
26. M. F. Krummel and J. P. Allison, CD28 and CTLA-4 have opposing effects on the response of T cells to stimulation, *J. Exp. Med.* 182 (1995) 459-465.
27. T. L. Walunas, D. J. Lenschow, C. Y. Bakker, P. S. Linsley, G. J. Freeman, J. M. Green, C. B. Thompson and J. A. Bluestone, CTLA-4 can function as a negative regulator of T cell activation, *Immunity* 1 (1994) 405-413.
28. J. Larkin, V. Chiarion-Sileni, R. Gonzalez, J. J. Grob, C. L. Cowey, C. D. Lao, D. Schadendorf, R. Dummer, M. Smylie, P. Rutkowski, P. F. Ferrucci, A. Hill, J. Wagstaff, M. S. Carlino, J. B. Haanen, M. Maio, I. Marquez-Rodas, G. A. McArthur, et al., Combined nivolumab and ipilimumab or monotherapy in untreated melanoma, *N. Engl. J. Med.* 373 (2015) 23-34.
29. A. G. Duffy, S. V. Ulahannan, O. Makorova-Rusher, O. Rahma, H. Wedemeyer, D. Pratt, J. L. Davis, M. S. Hughes, T. Heller, M. ElGindi, A. Uppala, F. Korangy, D. E. Kleiner, W. D. Figg, D. Venzon, S. M. Steinberg, A. M. Venkatesan, V. Krishnasamy, et al., Tremelimumab in combination with ablation in patients with advanced hepatocellular carcinoma, *J. Hepatol.* 66 (2017) 545-551.
30. N. A. Rizvi, B. C. Cho, N. Reinmuth, K. H. Lee, A. Luft, M.-J. Ahn, M. M. van den Heuvel, M. Cobo, D. Vicente, A. Smolin, V. Moiseyenko, S. J. Antonia, S. Le Moulec, G. Robinet, R. Natale, J. Schneider, F. A. Shepherd, S. L. Geater, et al., Durvalumab with or without tremelimumab vs standard chemotherapy in first-line treatment of metastatic non-small cell lung cancer: The MYSTIC phase 3 randomized clinical trial, *JAMA Oncol* 6 (2020) 661.
31. M. He, Y. Chai, J. Qi, C. W. H. Zhang, Z. Tong, Y. Shi, J. Yan, S. Tan and G. F. Gao, Remarkably similar CTLA-4 binding properties of therapeutic ipilimumab and tremelimumab antibodies, *Oncotarget* 8 (2017) 67129-67139.
32. J. Y. Lee, H. T. Lee, W. Shin, J. Chae, J. Choi, S. H. Kim, H. Lim, T. Won Heo, K. Y. Park, Y. J. Lee, S. E. Ryu, J. Y. Son, J. U. Lee and Y.-S. Heo, Structural basis of checkpoint blockade by monoclonal antibodies in cancer immunotherapy, *Nat Commun* 7 (2016) 13354.
33. L. Tang, H. Gao, X. Zhu, X. Wang, M. Zhou and R. Jiang, Construction of "small-intelligent" focused mutagenesis libraries using well-designed combinatorial degenerate primers, *BioTechniques* 52 (2012) 149-158.
34. M. T. Reetz and S. Wu, Greatly reduced amino acid alphabets in directed evolution: making the right choice for saturation mutagenesis at homologous enzyme positions, *Chem Commun* (Camb) (2008) 5499-5501.
35. M. A. Mena and P. S. Daugherty, Automated design of degenerate codon libraries, *Protein Eng. Des. Sel.* 18 (2005) 559-561.
36. W. M. Coco, RACHITT: Gene family shuffling by random chimeragenesis on transient templates, *Methods Mol. Biol.* 231 (2003) 111-127.
37. D. Lipovsek and A. Plückthun, In-vitro protein evolution by ribosome display and mRNA display, *Journal of Immunological Methods* 290 (2004) 51-67.

What is claimed:

1. A method of generating edited DNA comprising:
   a. amplifying a template via polymerase chain reaction (PCR) using a phosphorylated primer, a nonphosphorylated primer, and a DNA polymerase capable of incorporating deoxyuridine triphosphate (dUTP) to generate a deoxyuridine (dU)-containing amplicon;
   b. digesting the dU-containing amplicon of step (a) to degrade the phosphorylated strand and produce a single-stranded, dU-containing template;
   c. annealing at least one mutagenic primer to the template of step (b), wherein the at least one mutagenic primer is 5' phosphorylated single-stranded DNA comprising a region being edited flanked on each side by at least 10 bases that are complementary to the template, and wherein the region being edited comprises at least one mutation relative to the complement of the template;
   d. extending the mutagenic primers annealed in step (c) using a DNA polymerase that can read through uracil present in DNA and lacks 3'-exonuclease activity, 5'-exonuclease activity, and strand displacement activity to produce an extension product;
   e. ligating the extension product of step (d) to produce a partially mismatched double-stranded DNA product comprising a ligated edited strand and the dU-containing template;
   f. amplifying the ligated edited strand of step (e) using a forward primer, a reverse primer, and a DNA polymerase that is not able to read through uracil present in DNA and has an error rate at least 40 times lower than Taq polymerase.

2. The method of claim 1, wherein the dU-containing amplicon produced by step (a) is purified before the amplicon is used in step (b).

3. The method of claim 1, wherein step (b) is performed using a lambda (λ) exonuclease.

4. The method of claim 1, wherein the template produced in step (b) is purified before the template is used in step (c).

5. The method of claim 1, wherein at least one mutagenic primer annealed in step (c) contains more than one mutation relative to the complement of the template.

6. The method of claim 1, wherein more than one mutagenic primer is annealed in step (c).

7. The method of claim 6, wherein the mutagenic primers anneal at disparate regions of the template.

8. The method of claim 1, wherein step (c) is performed at room temperature.

9. The method of claim 1, wherein step (c) further comprises annealing a non-mutagenic primer to the 3' end of the template.

10. The method of claim 1, further comprising digesting the double-stranded DNA product of step (e) to remove the dU-containing template.

11. The method of claim 10, wherein digestion is performed using uracil-DNA glycosylate.

12. The method of claim 1, wherein the DNA polymerase used in step (a), and/or (d) is a high-fidelity DNA polymerase.

* * * * *

SEQUENCE LISTING

<160> NUMBER OF SEQ ID NOS: 54

<210> SEQ ID NO 1
<211> LENGTH: 43
<212> TYPE: DNA
<213> ORGANISM: Artificial Sequence
<220> FEATURE:
<223> OTHER INFORMATION: Synthetic - Mutagenic primer

<400> SEQUENCE: 1
cgttctccga gcgtacctgg rrkgtgctcc tgtccgtttg ccg      43

<210> SEQ ID NO 2
<211> LENGTH: 58
<212> TYPE: DNA
<213> ORGANISM: Artificial Sequence
<220> FEATURE:
<223> OTHER INFORMATION: Synthetic - Mutagenic primer
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 2
gtctggcagt aaacactatc vnavnacatt tgdscvdsct aaacatgctc caccgtcg      58

<210> SEQ ID NO 3
<211> LENGTH: 48
<212> TYPE: DNA
<213> ORGANISM: Artificial Sequence
<220> FEATURE:
<223> OTHER INFORMATION: Synthetic - Mutagenic primer
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 3
gcagtaaaca ctatcvnavn acatttgdsc vdsctaaaca tgctccac      48

<210> SEQ ID NO 4
<211> LENGTH: 51
<212> TYPE: DNA
<213> ORGANISM: Artificial Sequence
<220> FEATURE:
<223> OTHER INFORMATION: Synthetic - Mutagenic primer

<400> SEQUENCE: 4
gatcgccagg cgttcbmaga gvvtacctgg vravdkctcc tgtccgtttg c      51

<210> SEQ ID NO 5
<211> LENGTH: 54
<212> TYPE: DNA
<213> ORGANISM: Artificial Sequence
<220> FEATURE:
<223> OTHER INFORMATION: Synthetic - Mutagenic primer

<400> SEQUENCE: 5
ggctcgcggt ctggcagtaa vwactatcct gwvacatttg gcccagctaa acat      54

```
<210> SEQ ID NO 6
<211> LENGTH: 43
<212> TYPE: DNA
<213> ORGANISM: Artificial Sequence
<220> FEATURE:
<223> OTHER INFORMATION: Synthetic - Mutagenic primer

<400> SEQUENCE: 6
ataacaccct gttacgcgta rvtgaaattg ccaggattcg gat            43

<210> SEQ ID NO 7
<211> LENGTH: 43
<212> TYPE: DNA
<213> ORGANISM: Artificial Sequence
<220> FEATURE:
<223> OTHER INFORMATION: Synthetic - Mutagenic primer

<400> SEQUENCE: 7
ccaaggatgg ctctggtcag cratacctgg cctggtctgg gca            43

<210> SEQ ID NO 8
<211> LENGTH: 29
<212> TYPE: DNA
<213> ORGANISM: Artificial Sequence
<220> FEATURE:
<223> OTHER INFORMATION: Synthetic - Mutagenic primer

<400> SEQUENCE: 8
cctgatggat atgctcaggg atcgccagg                            29

<210> SEQ ID NO 9
<211> LENGTH: 35
<212> TYPE: DNA
<213> ORGANISM: Artificial Sequence
<220> FEATURE:
<223> OTHER INFORMATION: Synthetic - Mutagenic primer

<400> SEQUENCE: 9
ctcgcaagaa cctgatgatg tgctcaggga tcgcc                     35

<210> SEQ ID NO 10
<211> LENGTH: 37
<212> TYPE: DNA
<213> ORGANISM: Artificial Sequence
<220> FEATURE:
<223> OTHER INFORMATION: Synthetic - Mutagenic primer

<400> SEQUENCE: 10
ctcgcaagaa cctgatggat cgtgctcagg gatcgcc                   37

<210> SEQ ID NO 11
<211> LENGTH: 43
<212> TYPE: DNA
<213> ORGANISM: Artificial Sequence
<220> FEATURE:
<223> OTHER INFORMATION: Synthetic - Mutagenic primer

<400> SEQUENCE: 11
ggctcgcaag aacctgatgg atcacatgca agtgctcagg gat            43

<210> SEQ ID NO 12
<211> LENGTH: 41
<212> TYPE: DNA
<213> ORGANISM: Artificial Sequence
<220> FEATURE:
<223> OTHER INFORMATION: Synthetic - Mutagenic primer
```

<400> SEQUENCE: 12
ggctcgcaag aacctgatgg atgatcgcca ggcgttctcc g        41

<210> SEQ ID NO 13
<211> LENGTH: 44
<212> TYPE: DNA
<213> ORGANISM: Artificial Sequence
<220> FEATURE:
<223> OTHER INFORMATION: Synthetic - Mutagenic primer

<400> SEQUENCE: 13
gaggctcgca agaacctgat gagggtgctc agggatcgcc aggc        44

<210> SEQ ID NO 14
<211> LENGTH: 43
<212> TYPE: DNA
<213> ORGANISM: Artificial Sequence
<220> FEATURE:
<223> OTHER INFORMATION: Synthetic - Mutagenic primer

<400> SEQUENCE: 14
catggtgcaa gttgaacaac accaaatggt ttcccgcgga acc        43

<210> SEQ ID NO 15
<211> LENGTH: 43
<212> TYPE: DNA
<213> ORGANISM: Artificial Sequence
<220> FEATURE:
<223> OTHER INFORMATION: Synthetic - Mutagenic primer

<400> SEQUENCE: 15
ctatcctgca acatttggcc atactaaaca tgctccaccg tcg        43

<210> SEQ ID NO 16
<211> LENGTH: 43
<212> TYPE: DNA
<213> ORGANISM: Artificial Sequence
<220> FEATURE:
<223> OTHER INFORMATION: Synthetic - Mutagenic primer

<400> SEQUENCE: 16
cgaatccgaa gggagaacgt atctgctggt gagcgtacga agc        43

<210> SEQ ID NO 17
<211> LENGTH: 43
<212> TYPE: DNA
<213> ORGANISM: Artificial Sequence
<220> FEATURE:
<223> OTHER INFORMATION: Synthetic - Mutagenic primer

<400> SEQUENCE: 17
agcgaacggg gccaggatat gtctactctg gcatttctgg ggg        43

<210> SEQ ID NO 18
<211> LENGTH: 35
<212> TYPE: DNA
<213> ORGANISM: Artificial Sequence
<220> FEATURE:
<223> OTHER INFORMATION: Synthetic - Mutagenic primer

<400> SEQUENCE: 18
ctccgagcgt acctggaaaa ctctcctgtc cgttt        35

<210> SEQ ID NO 19
<211> LENGTH: 43

-continued

```
<212> TYPE: DNA
<213> ORGANISM: Artificial Sequence
<220> FEATURE:
<223> OTHER INFORMATION: Synthetic - Mutagenic primer

<400> SEQUENCE: 19
cgtacctgga aagtgctcct acgcgtttgc cggacgtggg cgg                   43

<210> SEQ ID NO 20
<211> LENGTH: 46
<212> TYPE: DNA
<213> ORGANISM: Artificial Sequence
<220> FEATURE:
<223> OTHER INFORMATION: Synthetic - Mutagenic primer

<400> SEQUENCE: 20
catgtagagc ttctcagtct sttrrtagtt atctggattg gtacca               46

<210> SEQ ID NO 21
<211> LENGTH: 49
<212> TYPE: DNA
<213> ORGANISM: Artificial Sequence
<220> FEATURE:
<223> OTHER INFORMATION: Synthetic - Mutagenic primer

<400> SEQUENCE: 21
ctcccaaact gctcatctac gscgcttytt ctttgcagag cggcgtgcc            49

<210> SEQ ID NO 22
<211> LENGTH: 55
<212> TYPE: DNA
<213> ORGANISM: Artificial Sequence
<220> FEATURE:
<223> OTHER INFORMATION: Synthetic - Mutagenic primer

<400> SEQUENCE: 22
catactattg ccagcagtac krttcawcac cctkkacttt tgggcccgga acaaa    55

<210> SEQ ID NO 23
<211> LENGTH: 43
<212> TYPE: DNA
<213> ORGANISM: Artificial Sequence
<220> FEATURE:
<223> OTHER INFORMATION: Synthetic - Mutagenic primer

<400> SEQUENCE: 23
gatttacttt ctcaagctat rstatgcact gggttcgcca agc                   43

<210> SEQ ID NO 24
<211> LENGTH: 52
<212> TYPE: DNA
<213> ORGANISM: Artificial Sequence
<220> FEATURE:
<223> OTHER INFORMATION: Synthetic - Mutagenic primer

<400> SEQUENCE: 24
gaaagggctt ggaatgggtg rccktcatct sgtatgacgg atccaacaaa ta        52

<210> SEQ ID NO 25
<211> LENGTH: 46
<212> TYPE: DNA
<213> ORGANISM: Artificial Sequence
<220> FEATURE:
<223> OTHER INFORMATION: Synthetic - Mutagenic primer

<400> SEQUENCE: 25
```
cggtctacta ctgtgccagg rmtssacgcg gcgcaaccct gtacta        46

<210> SEQ ID NO 26
<211> LENGTH: 52
<212> TYPE: DNA
<213> ORGANISM: Artificial Sequence
<220> FEATURE:
<223> OTHER INFORMATION: Synthetic - Mutagenic primer

<400> SEQUENCE: 26
gcggcgcaac cctgtactat trstrtkrts scatggatgt ttggggacaa gg        52

<210> SEQ ID NO 27
<211> LENGTH: 46
<212> TYPE: DNA
<213> ORGANISM: Artificial Sequence
<220> FEATURE:
<223> OTHER INFORMATION: Synthetic - Starting sequence

<400> SEQUENCE: 27
ggcgttctcc gagcgtacct ggaaagtgct cctgtccgtt tgccgg        46

<210> SEQ ID NO 28
<211> LENGTH: 65
<212> TYPE: DNA
<213> ORGANISM: Artificial Sequence
<220> FEATURE:
<223> OTHER INFORMATION: Synthetic - Starting sequence

<400> SEQUENCE: 28
gcggtctggc agtaaacact atcctgcaac atttggccca gctaaacatg ctccaccgtc        60
ggttc        65

<210> SEQ ID NO 29
<211> LENGTH: 671
<212> TYPE: DNA
<213> ORGANISM: Artificial Sequence
<220> FEATURE:
<223> OTHER INFORMATION: Synthetic - Top strand of wild-type scFv gene

<400> SEQUENCE: 29
gtgcagcctc aggatttact ttctcaagct atggtatgca ctgggttcgc caagctcccg        60
gaaagggctt ggaatgggtg gccgtaatct ggtatgacgg atccaacaaa tattatgcag        120
actctgttaa agggcgcttt actatttccc gggacaactc caagaataca ctgtacctgc        180
agatgaacag cctgcgggcc gaagacacag cggtctacta ctgtgccagg gaccctcgcg        240
gcgcaaccct gtactattac tattatggca tggatgtttg gggacaagga acgaccgtta        300
cagtcagtag tggcggtgga ggttcaggtg gaggaggctc aggtggaggc ggctccgata        360
ttcaaatgac tcagtcccct tcttctctga gcgcctctgt gggcgatcgc gtgactataa        420
catgtagagc ttctcagtct attaatagtt atctggattg gtaccaacag aagcccggca        480
aggctcccaa actgctcatc tacgctgctt cctctttgca gagcggcgtg ccttctaggt        540
tctctggatc tgggagtgga actgacttta cgctcacgat tagctccctt cagccagaag        600
acttcgcgac atactattgc cagcagtact attcaacacc ctttactttt gggcccggaa        660
caaaggttga a        671

<210> SEQ ID NO 30
<211> LENGTH: 671
<212> TYPE: DNA
<213> ORGANISM: Artificial Sequence

```
<220> FEATURE:
<223> OTHER INFORMATION: Synthetic - Bottom strand of wild-type scFv
      gene

<400> SEQUENCE: 30
cacgtcggag tcctaaatga aagagttcga taccatacgt gacccaagcg gttcgagggc    60
cttccccgaa ccttacccac cggcattaga ccatactgcc taggttgttt ataatacgtc   120
tgagacaatt tcccgcgaaa tgataaaggg ccctgttgag gttcttatgt gacatggacg   180
tctacttgtc ggacgccgg cttctgtgtc gccagatgat gacacggtcc ctgggagcgc   240
cgcgttggga catgataatg ataataccgt acctacaaac ccctgttcct tgctggcaat   300
gtcagtcatc accgccacct ccaagtccac ctcctccgag tccacctccg ccgaggctat   360
aagtttactg agtcagggga agaagagact cgcggagaca cccgctagcg cactgatatt   420
gtacatctcg aagagtcaga taattatcaa tagacctaac catggttgtc ttcgggccgt   480
tccgagggtt tgacgagtag atgcgacgaa ggagaaacgt ctcgccgcac ggaagatcca   540
agagacctag accctcacct tgactgaaat gcgagtgcta atcgagggaa gtcggtcttc   600
tgaagcgctg tatgataacg gtcgtcatga taagttgtgg gaaatgaaaa cccgggcctt   660
gtttccaact t                                                        671

<210> SEQ ID NO 31
<211> LENGTH: 30
<212> TYPE: DNA
<213> ORGANISM: Artificial Sequence
<220> FEATURE:
<223> OTHER INFORMATION: Synthetic - Mutagenic primer

<400> SEQUENCE: 31
gatcgccagg cgttcbmaga gvvtacctgg                                     30

<210> SEQ ID NO 32
<211> LENGTH: 30
<212> TYPE: DNA
<213> ORGANISM: Artificial Sequence
<220> FEATURE:
<223> OTHER INFORMATION: Synthetic - Starting sequence

<400> SEQUENCE: 32
agggatcgcc aggcgttctc cgagcgtacc                                     30

<210> SEQ ID NO 33
<211> LENGTH: 30
<212> TYPE: DNA
<213> ORGANISM: Artificial Sequence
<220> FEATURE:
<223> OTHER INFORMATION: Synthetic - Mutagenic primer

<400> SEQUENCE: 33
ggctcgcggt ctggcagtaa vwactatcct                                     30

<210> SEQ ID NO 34
<211> LENGTH: 30
<212> TYPE: DNA
<213> ORGANISM: Artificial Sequence
<220> FEATURE:
<223> OTHER INFORMATION: Synthetic - Starting sequence

<400> SEQUENCE: 34
caggctcgcg gtctggcagt aaacactatc                                     30
```

-continued

```
<210> SEQ ID NO 35
<211> LENGTH: 30
<212> TYPE: DNA
<213> ORGANISM: Artificial Sequence
<220> FEATURE:
<223> OTHER INFORMATION: Synthetic - Mutagenic primer

<400> SEQUENCE: 35
ataacaccct gttacgcgta rvtgaaattg                                    30

<210> SEQ ID NO 36
<211> LENGTH: 30
<212> TYPE: DNA
<213> ORGANISM: Artificial Sequence
<220> FEATURE:
<223> OTHER INFORMATION: Synthetic - Starting sequence

<400> SEQUENCE: 36
cttataacac cctgttacgc gtatccgaaa                                    30

<210> SEQ ID NO 37
<211> LENGTH: 30
<212> TYPE: DNA
<213> ORGANISM: Artificial Sequence
<220> FEATURE:
<223> OTHER INFORMATION: Synthetic - Mutagenic primer

<400> SEQUENCE: 37
ccaaggatgg ctctggtcag cratacctgg                                    30

<210> SEQ ID NO 38
<211> LENGTH: 30
<212> TYPE: DNA
<213> ORGANISM: Artificial Sequence
<220> FEATURE:
<223> OTHER INFORMATION: Synthetic - Starting sequence

<400> SEQUENCE: 38
ggtgccaagg atggctctgg tcagagatac                                    30

<210> SEQ ID NO 39
<211> LENGTH: 37
<212> TYPE: DNA
<213> ORGANISM: Artificial Sequence
<220> FEATURE:
<223> OTHER INFORMATION: Synthetic - Starting sequence

<400> SEQUENCE: 39
gaggctcgca agaacctgat ggatgtgctc agggatc                            37

<210> SEQ ID NO 40
<211> LENGTH: 46
<212> TYPE: DNA
<213> ORGANISM: Artificial Sequence
<220> FEATURE:
<223> OTHER INFORMATION: Synthetic - Resulting sequence

<400> SEQUENCE: 40
gaggctcgca agaacctgat ggatcacatg caagtgctca gggatc                  46

<210> SEQ ID NO 41
<211> LENGTH: 53
<212> TYPE: DNA
<213> ORGANISM: Artificial Sequence
<220> FEATURE:
<223> OTHER INFORMATION: Synthetic - Starting sequence
```

<400> SEQUENCE: 41
gaggctcgca agaacctgat ggatgtgctc agggatcgcc aggcgttctc cga            53

<210> SEQ ID NO 42
<211> LENGTH: 44
<212> TYPE: DNA
<213> ORGANISM: Artificial Sequence
<220> FEATURE:
<223> OTHER INFORMATION: Synthetic - Resulting sequence

<400> SEQUENCE: 42
gaggctcgca agaacctgat ggatgatcgc caggcgttct ccga                    44

<210> SEQ ID NO 43
<211> LENGTH: 550
<212> TYPE: DNA
<213> ORGANISM: P1 bacteriophage
<220> FEATURE:
<221> NAME/KEY: misc_feature
<222> LOCATION: (1)..(550)
<223> OTHER INFORMATION: Top strand of Cre recombinase gene

<400> SEQUENCE: 43
atgtcaatac tactgacctt gcaccaaagt ttgtccgcat tactggtcga tgcaacgagt     60
gatgaggctc gcaagaacct gatggatgtg ctcagggatc gccaggcgtt ctccgagcgt    120
acctggaaag tgctcctgtc cgtttgccgg acgtgggcgg catggtgcaa gttgaacaac    180
cggaaatggt tcccgcgga acctgaagat gttcgcgatt accttctaca tcttcaggct    240
cgcggtctgg cagtaaacac tatcctgcaa catttggccc agctaaacat gctccaccgt    300
cggttcgggc tgccacgacc gggcgacagc gacgctgttt cactggttat gcggcgaatc    360
cgaagggaga acgtcgatgc tggtgagcgt acgaagcagg ccctagcgtt cgagcgcact    420
gacttcgacc aggttcgtgc actcatggaa aatagcgaac ggggccagga tatacgtact    480
ctggcatttc tggggggttgc ttataacacc ctgttacgcg tatccgaaat tgccaggatt    540
cggattaaag                                                           550

<210> SEQ ID NO 44
<211> LENGTH: 550
<212> TYPE: DNA
<213> ORGANISM: P1 bacteriophage
<220> FEATURE:
<221> NAME/KEY: misc_feature
<222> LOCATION: (1)..(550)
<223> OTHER INFORMATION: Bottom strand of Cre recombinase gene

<400> SEQUENCE: 44
tacagttatg atgactggaa cgtggtttca aacaggcgta atgaccagct acgttgctca     60
ctactccgag cgttcttgga ctacctacac gagtccctag cggtccgcaa gaggctcgca    120
tggacctttc acgaggacag gcaaacggcc tgcacccgcc gtaccacgtt caacttgttg    180
gcctttacca aagggcgcct ggacttcta caagcgctaa tggaagatgt agaagtccga    240
gcgccagacc gtcatttgtg ataggacgtt gtaaaccggg tcgatttgta cgaggtggca    300
gccaagcccg acggtgctgg cccgctgtcg ctgcgacaaa gtgaccaata cgccgcttag    360
gcttccctct tgcagctacg accactcgca tgcttcgtcc gggatcgcaa gctcgcgtga    420
ctgaagctgg tccaagcacg tgagtacctt ttatcgcttg ccccggtcct atatgcatga    480
gaccgtaaag acccccaacg aatattgtgg gacaatgcgc ataggcttta acggtcctaa    540
gcctaatttc                                                           550

<210> SEQ ID NO 45
<211> LENGTH: 46
<212> TYPE: DNA
<213> ORGANISM: Artificial Sequence
<220> FEATURE:
<223> OTHER INFORMATION: Synthetic - Mutagenic primer

<400> SEQUENCE: 45
cggtctacta ctgttccagg rmtssacgcg gcgcaaccct gtacta                    46

<210> SEQ ID NO 46
<211> LENGTH: 50
<212> TYPE: DNA
<213> ORGANISM: Artificial Sequence
<220> FEATURE:
<223> OTHER INFORMATION: Synthetic - Starting sequence

<400> SEQUENCE: 46
agcggtctac tactgttcca gggaccctcg cggcgcaacc ctgtactatt                50

<210> SEQ ID NO 47
<211> LENGTH: 49
<212> TYPE: DNA
<213> ORGANISM: Artificial Sequence
<220> FEATURE:
<223> OTHER INFORMATION: Synthetic - Starting sequence

<400> SEQUENCE: 47
acatgtagag cttctcagtc tattaatagt tatctggatt ggtaccaac                 49

<210> SEQ ID NO 48
<211> LENGTH: 48
<212> TYPE: DNA
<213> ORGANISM: Artificial Sequence
<220> FEATURE:
<223> OTHER INFORMATION: Synthetic - Mutagenic primer

<400> SEQUENCE: 48
ctcccaaact gctcatctac gscgcttytt cttgcagagc ggcgtgcc                  48

<210> SEQ ID NO 49
<211> LENGTH: 51
<212> TYPE: DNA
<213> ORGANISM: Artificial Sequence
<220> FEATURE:
<223> OTHER INFORMATION: Synthetic - Starting sequence

<400> SEQUENCE: 49
ggctcccaaa ctgctcatct acgctgcttc ctcttgcaga gcggcgtgcc t              51

<210> SEQ ID NO 50
<211> LENGTH: 55
<212> TYPE: DNA
<213> ORGANISM: Artificial Sequence
<220> FEATURE:
<223> OTHER INFORMATION: Synthetic - Mutagenic primer

<400> SEQUENCE: 50
catactattg ccagcagtac krttcawcaa cctkkacttt tgggcccgga acaaa          55

<210> SEQ ID NO 51
<211> LENGTH: 57
<212> TYPE: DNA
<213> ORGANISM: Artificial Sequence
<220> FEATURE:

```
<223> OTHER INFORMATION: Synthetic - Starting sequence

<400> SEQUENCE: 51
gacatactat tgccagcagt actattcaac aacctttact tttgggcccg gaacaaa        57

<210> SEQ ID NO 52
<211> LENGTH: 54
<212> TYPE: DNA
<213> ORGANISM: Artificial Sequence
<220> FEATURE:
<223> OTHER INFORMATION: Synthetic - Mutagenic primer

<400> SEQUENCE: 52
tcgcggcgca accctgtact attrstrtkr tsscatggat gtttggggac aagg           54

<210> SEQ ID NO 53
<211> LENGTH: 55
<212> TYPE: DNA
<213> ORGANISM: Artificial Sequence
<220> FEATURE:
<223> OTHER INFORMATION: Synthetic - Starting sequence

<400> SEQUENCE: 53
tcgcggcgca accctgtact attactatta tggcatggat gtttggggac aagga          55

<210> SEQ ID NO 54
<211> LENGTH: 103
<212> TYPE: DNA
<213> ORGANISM: Artificial Sequence
<220> FEATURE:
<223> OTHER INFORMATION: Synthetic - Starting sequence

<400> SEQUENCE: 54
aggatttact ttctcaagct atggtatgca ctgggttcgc caagctcccg gaaagggctt     60
ggaatgggtg gccgtaatct ggtatgacgg atccaacaaa tat                      103
```